(12) United States Patent
Orphanos et al.

(10) Patent No.: US 9,943,328 B2
(45) Date of Patent: *Apr. 17, 2018

(54) UNITARY ENDOSCOPIC VESSEL HARVESTING DEVICES WITH AN ELASTIC FORCE

(71) Applicant: Saphena Medical, Inc., West Bridgewater, MA (US)

(72) Inventors: Mark J. Orphanos, Foxboro, MA (US); Albert K. Chin, Palo Alto, CA (US); Michael Glennon, Norwell, MA (US)

(73) Assignee: Saphena Medical, Inc., West Bridgewater, MA (US)

(*) Notice: Subject to any disclaimer, the term of this patent is extended or adjusted under 35 U.S.C. 154(b) by 408 days.

This patent is subject to a terminal disclaimer.

(21) Appl. No.: 14/697,972

(22) Filed: Apr. 28, 2015

(65) Prior Publication Data

US 2016/0317171 A1    Nov. 3, 2016

(51) Int. Cl.
*A61B 18/14* (2006.01)
*A61B 17/3205* (2006.01)
(Continued)

(52) U.S. Cl.
CPC .... *A61B 17/3205* (2013.01); *A61B 17/00008* (2013.01); *A61B 17/32* (2013.01);
(Continued)

(58) Field of Classification Search
CPC  A61B 2018/00196; A61B 2018/00202; A61B 2018/00404; A61B 2018/00601;
(Continued)

(56) References Cited

U.S. PATENT DOCUMENTS 5,373,840 A   12/1994   Knighton
5,556,408 A    9/1996   Farhat
(Continued)

FOREIGN PATENT DOCUMENTS

EP   1570787   9/2005
EP   2364653   9/2011
(Continued)

OTHER PUBLICATIONS

International Search Report and Written Opinion issued in International Application No. PCT/US2014/018737 dated Jun. 18, 2014.
(Continued)

*Primary Examiner* — Jaymi Della
(74) *Attorney, Agent, or Firm* — Greenberg Traurig, LLP; Chinh H. Pham; Roman Fayerberg

(57) ABSTRACT

Unitary endoscopic vessel harvesting devices with an elastic force are disclosed. In some embodiments, such devices comprise an elongated body having a proximal end and a distal end, a tip disposed at the distal end of the elongated body; and cutting unit having an elastic force, a first cutting portion and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel, and a biasing member engaged with the cutting unit to bias at least one cutting portion toward the other cutting portion.

15 Claims, 26 Drawing Sheets

(51) Int. Cl.
*A61B 17/00* (2006.01)
*A61B 17/32* (2006.01)
*A61B 90/00* (2016.01)
*A61B 18/00* (2006.01)

(52) U.S. Cl.
CPC .... *A61B 17/32002* (2013.01); *A61B 18/1445* (2013.01); *A61B 90/37* (2016.02); *A61B 2017/00778* (2013.01); *A61B 2017/00902* (2013.01); *A61B 2017/00969* (2013.01); *A61B 2017/320064* (2013.01); *A61B 2018/00428* (2013.01); *A61B 2018/00601* (2013.01); *A61B 2018/1457* (2013.01)

(58) Field of Classification Search
CPC ...... A61B 2018/126; A61B 2018/1415; A61B 2018/1422; A61B 2018/1425; A61B 2018/1427; A61B 2018/1475; A61B 18/1445; A61B 17/32002; A61B 17/32; A61B 2018/00428; A61B 2017/320064; A61B 2017/00778; A61B 2018/1457; A61B 2017/00969; A61B 2017/00902; A61B 17/00008
See application file for complete search history.

(56) References Cited

U.S. PATENT DOCUMENTS

| | | |
|---|---|---|
| 5,591,183 A | 1/1997 | Chin |
| 5,676,636 A | 10/1997 | Chin |
| 5,695,514 A | 12/1997 | Chin |
| 5,728,123 A | 3/1998 | Lemelson et al. |
| 5,772,576 A | 6/1998 | Knighton et al. |
| 5,797,946 A | 8/1998 | Chin |
| 5,810,805 A * | 9/1998 | Sutcu ............... A61B 18/1442 606/45 |
| 5,823,946 A | 10/1998 | Chin |
| 5,873,889 A | 2/1999 | Chin |
| 5,891,141 A | 4/1999 | Rydell |
| 5,895,353 A | 4/1999 | Lunsford et al. |
| 5,916,233 A | 6/1999 | Chin |
| 5,921,919 A | 7/1999 | Chin et al. |
| 5,941,819 A | 8/1999 | Chin |
| 5,968,065 A | 10/1999 | Chin |
| 5,976,168 A | 11/1999 | Chin |
| 5,980,549 A | 11/1999 | Chin |
| 5,984,937 A | 11/1999 | Morse et al. |
| 5,993,384 A | 11/1999 | Lunsford et al. |
| 6,030,406 A | 2/2000 | Davis et al. |
| 6,036,714 A | 3/2000 | Chin |
| 6,042,538 A | 3/2000 | Puskas |
| 6,102,909 A * | 8/2000 | Chen ............... A61B 17/2804 606/170 |
| 6,162,173 A | 12/2000 | Chin et al. |
| 6,176,825 B1 | 1/2001 | Chin et al. |
| 6,203,557 B1 | 3/2001 | Chin |
| 6,203,559 B1 | 3/2001 | Davis et al. |
| 6,264,670 B1 | 7/2001 | Chin |
| 6,277,137 B1 | 8/2001 | Chin |
| 6,348,037 B1 | 2/2002 | Chin et al. |
| 6,402,720 B1 | 6/2002 | Miller et al. |
| 6,406,425 B1 | 6/2002 | Chin et al. |
| 6,428,468 B1 | 8/2002 | Knighton et al. |
| 6,428,539 B1 | 8/2002 | Baxter et al. |
| 6,428,556 B1 | 8/2002 | Chin |
| 6,432,044 B1 | 8/2002 | Lunsford et al. |
| 6,471,638 B1 | 10/2002 | Chang et al. |
| 6,506,200 B1 | 1/2003 | Chin |
| 6,569,082 B1 | 5/2003 | Chin |
| 6,607,547 B1 | 8/2003 | Chin |
| 6,673,087 B1 | 1/2004 | Chang et al. |
| 6,702,813 B1 | 3/2004 | Baxter et al. |
| 6,706,052 B1 | 3/2004 | Chin |
| 6,749,609 B1 | 6/2004 | Lunsford et al. |
| 6,752,756 B2 | 6/2004 | Lunsford et al. |
| 6,811,546 B1 | 11/2004 | Callas et al. |
| 6,814,696 B1 | 11/2004 | Chang et al. |
| 6,830,546 B1 | 12/2004 | Chin et al. |
| 6,951,568 B1 | 10/2005 | Chin |
| 6,976,957 B1 | 12/2005 | Chin et al. |
| 7,001,404 B1 | 2/2006 | Chin |
| 7,033,357 B2 | 4/2006 | Baxter et al. |
| 7,066,875 B2 | 6/2006 | Knighton et al. |
| 7,214,180 B2 | 5/2007 | Chin |
| 7,264,587 B2 | 9/2007 | Chin |
| 7,276,075 B1 | 10/2007 | Callas et al. |
| 7,326,178 B1 | 3/2008 | Lunsford et al. |
| 7,344,536 B1 | 3/2008 | Lunsford et al. |
| 7,384,423 B1 | 6/2008 | Chin |
| 7,398,781 B1 | 7/2008 | Chin |
| 7,476,198 B1 | 1/2009 | Chin et al. |
| 7,485,092 B1 | 2/2009 | Stewart et al. |
| 7,534,243 B1 | 5/2009 | Chin et al. |
| 7,544,195 B2 | 6/2009 | Lunsford et al. |
| 7,556,633 B2 | 7/2009 | Lindsay |
| 7,645,289 B2 | 1/2010 | Bayer et al. |
| 7,695,470 B1 | 4/2010 | Stewart et al. |
| 7,867,163 B2 | 1/2011 | Chin et al. |
| 7,887,558 B2 | 2/2011 | Lin et al. |
| 7,918,848 B2 | 4/2011 | Lau et al. |
| 7,931,590 B2 | 4/2011 | Willis |
| 7,938,842 B1 | 5/2011 | Chin |
| 7,972,265 B1 | 7/2011 | Chin et al. |
| 7,981,133 B2 | 7/2011 | Chin |
| 8,075,559 B2 | 12/2011 | Stewart et al. |
| 8,083,664 B2 | 12/2011 | Davis |
| 8,197,472 B2 | 6/2012 | Lau et al. |
| 8,241,210 B2 | 8/2012 | Lunsford et al. |
| 8,372,096 B2 | 2/2013 | Kadykowski et al. |
| 8,414,480 B2 | 4/2013 | Kendale et al. |
| 8,460,331 B2 | 6/2013 | Chin |
| 8,623,003 B2 | 1/2014 | Lau et al. |
| 8,657,818 B2 | 2/2014 | Lin |
| 2004/0133228 A1 | 7/2004 | Bayer |
| 2004/0243167 A1 | 12/2004 | Tanaka et al. |
| 2005/0192613 A1* | 9/2005 | Lindsay ........... A61B 17/00008 606/190 |
| 2006/0095056 A1 | 5/2006 | Douglas et al. |
| 2008/0208192 A1* | 8/2008 | Kadykowski .... A61B 17/00008 606/46 |
| 2008/0306335 A1 | 12/2008 | Lau et al. |
| 2009/0023986 A1 | 1/2009 | Stewart et al. |
| 2010/0268175 A1 | 10/2010 | Lunsford et al. |
| 2012/0149983 A1 | 6/2012 | Chin |
| 2012/0289957 A1* | 11/2012 | Emmerich ......... A61B 18/1445 606/41 |
| 2013/0197299 A1 | 8/2013 | Chin et al. |
| 2013/0274548 A1 | 10/2013 | Fels et al. |
| 2014/0296847 A1 | 10/2014 | Chin et al. |
| 2014/0378957 A1 | 12/2014 | Orphanos et al. |
| 2015/0141938 A1 | 5/2015 | Pravongviengkham et al. |

FOREIGN PATENT DOCUMENTS

| | | |
|---|---|---|
| JP | 2000-505315 | 5/2000 |
| WO | 02/01998 | 1/2002 |
| WO | 03/013367 | 2/2003 |
| WO | 2004/043530 | 5/2004 |
| WO | 2006/127241 | 11/2006 |
| WO | 2009/148809 | 12/2009 |
| WO | 2011/130399 | 10/2011 |

OTHER PUBLICATIONS

PCT International Search Report and Written Opinion issued in International Application No. PCT/US2015/035266 dated Sep. 11, 2015.

Extended European Search Report issued in European Application No. 16163921.6 dated Sep. 19, 2016.

International Search Report and Written Opinion issued in International Application No. PCT/US2016/037873 dated Sep. 8, 2016.

(56) References Cited

OTHER PUBLICATIONS

Office Action for corresponding Japanese Patent Application No. 2016-500439, dated Aug. 22, 2017.
Extended European Search Report for corresponding European Patent Application No. 14773921, dated Feb. 17, 2017.

* cited by examiner

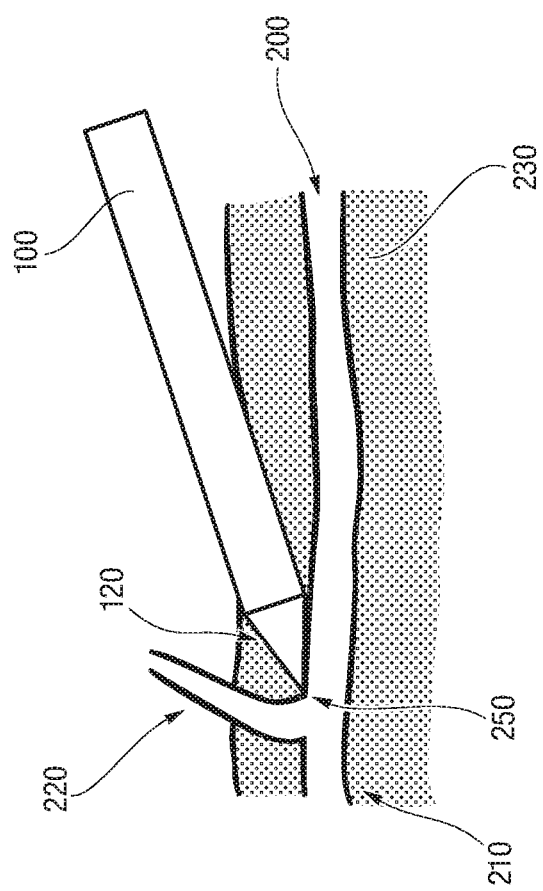

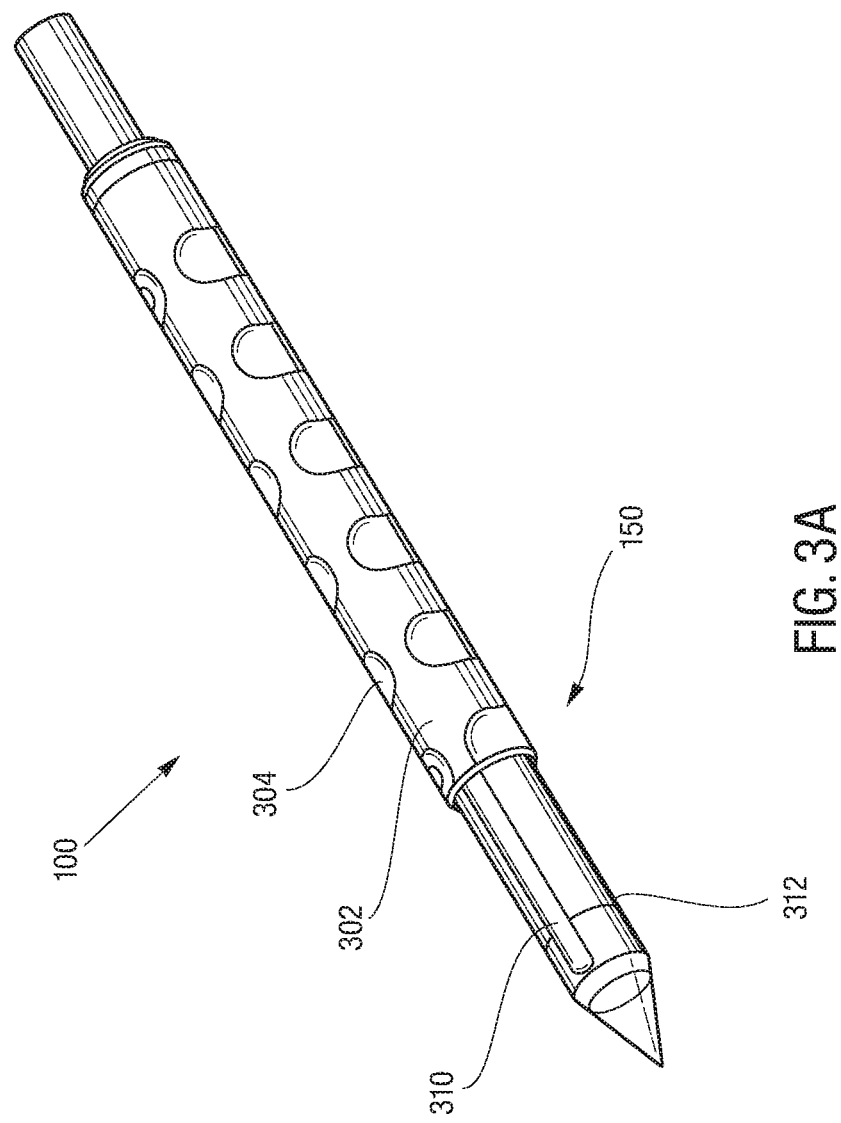

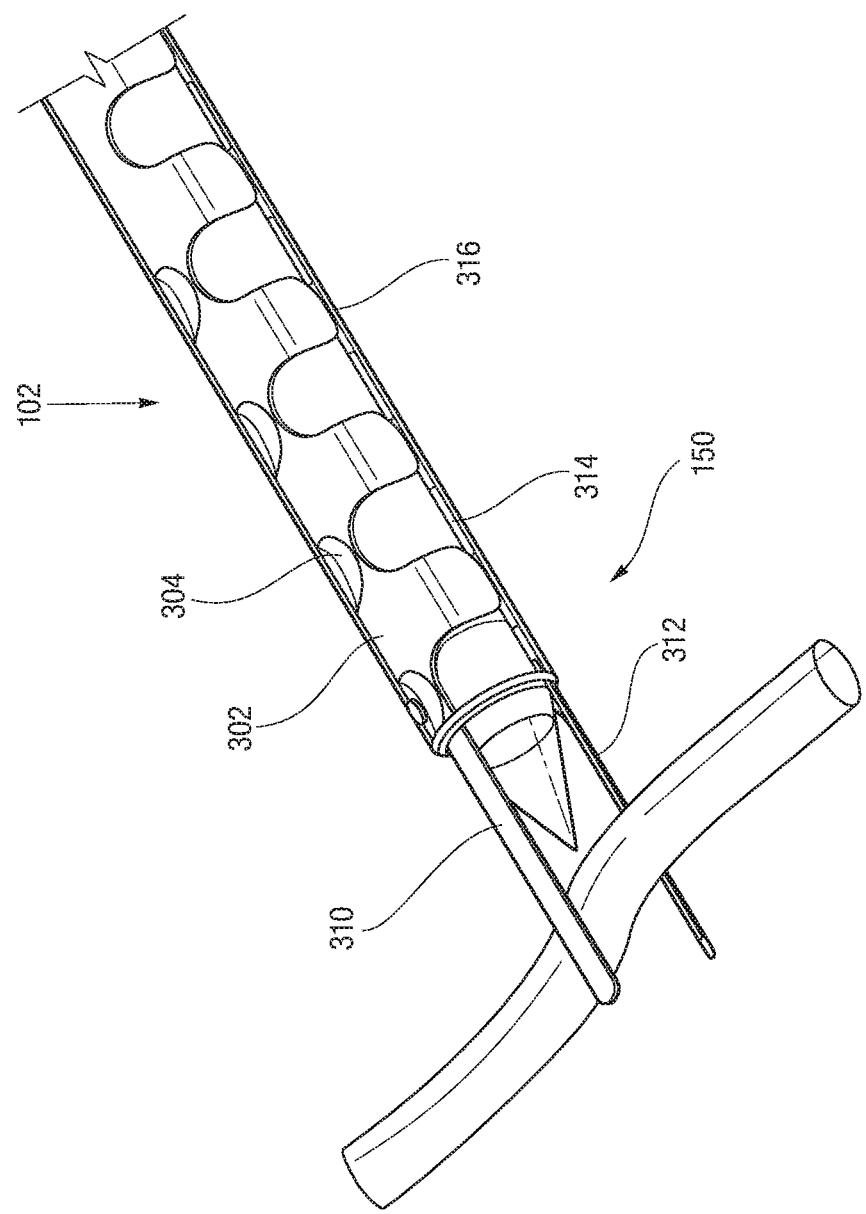

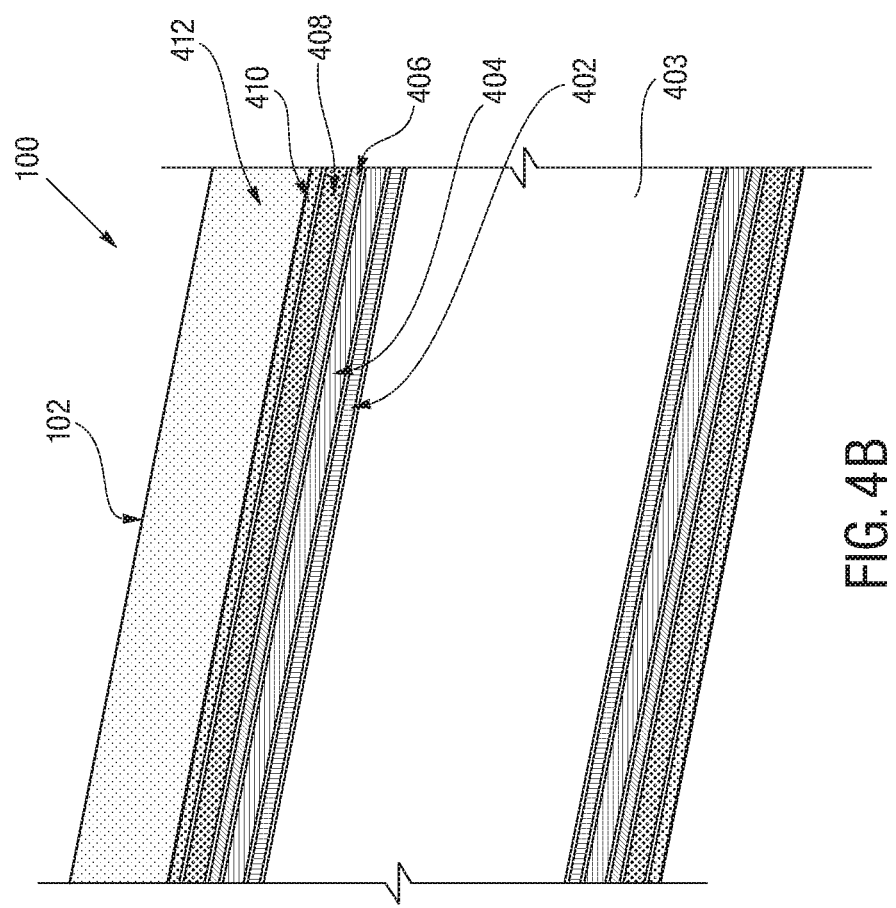

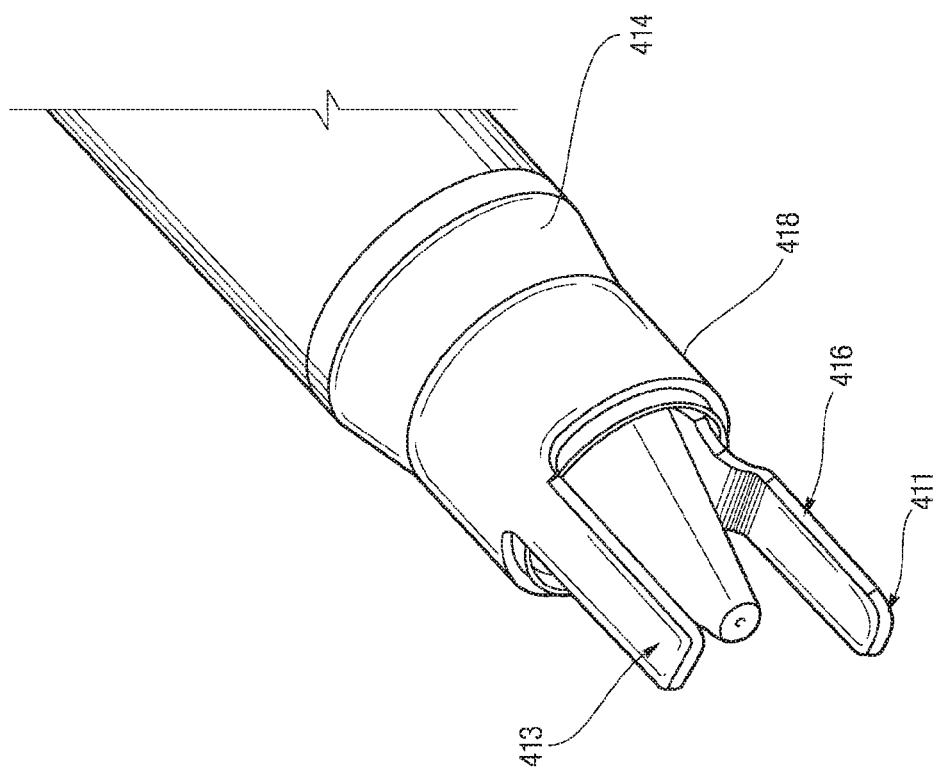

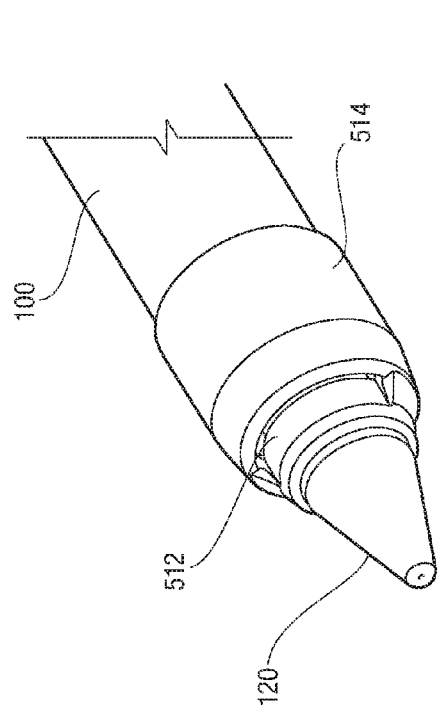
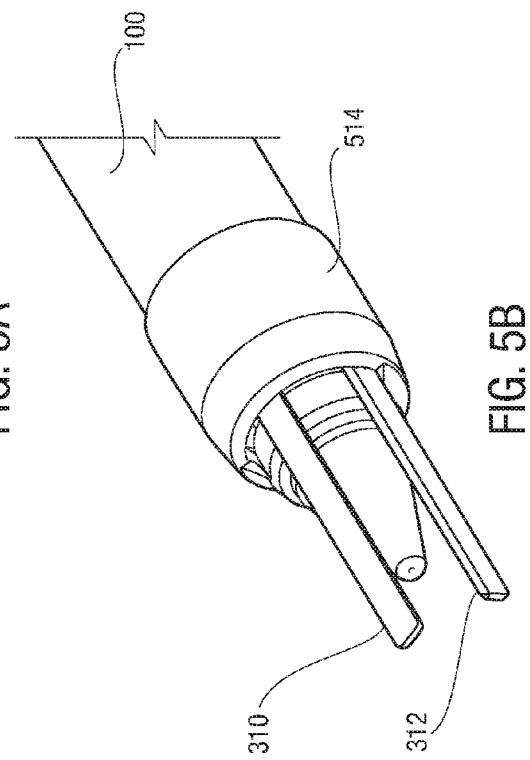
FIG. 5A
FIG. 5B

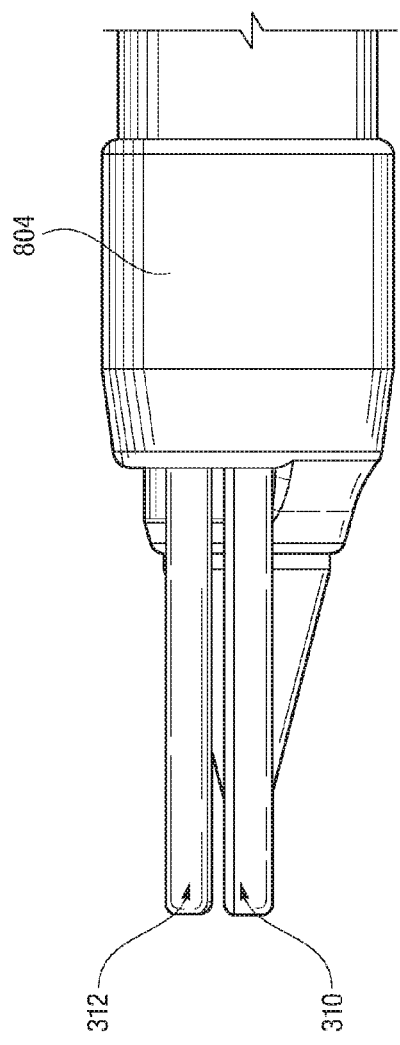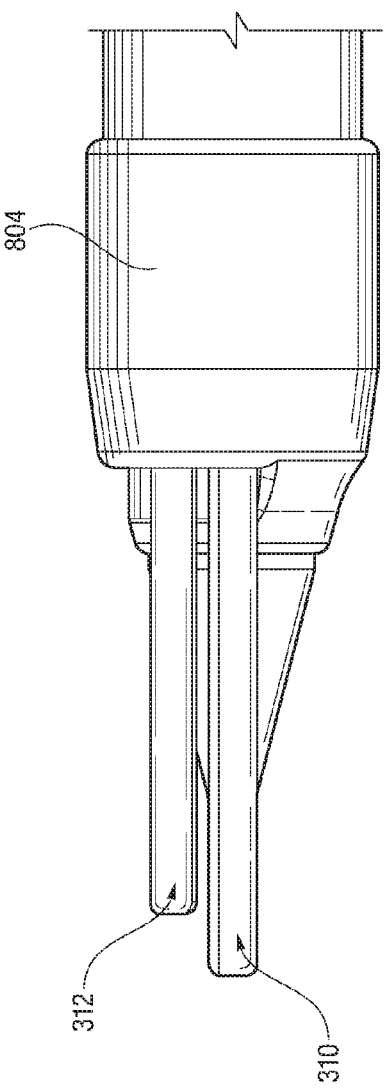

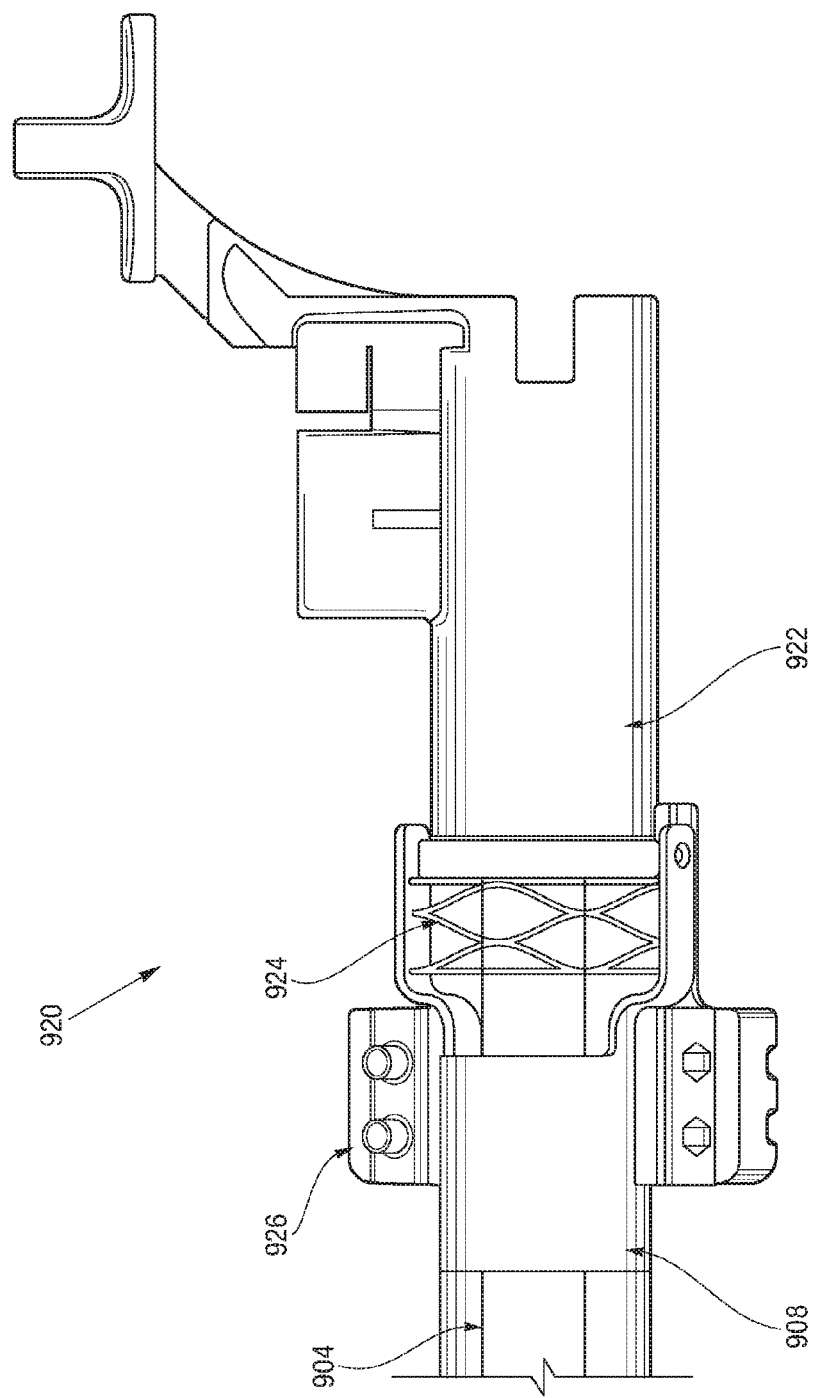

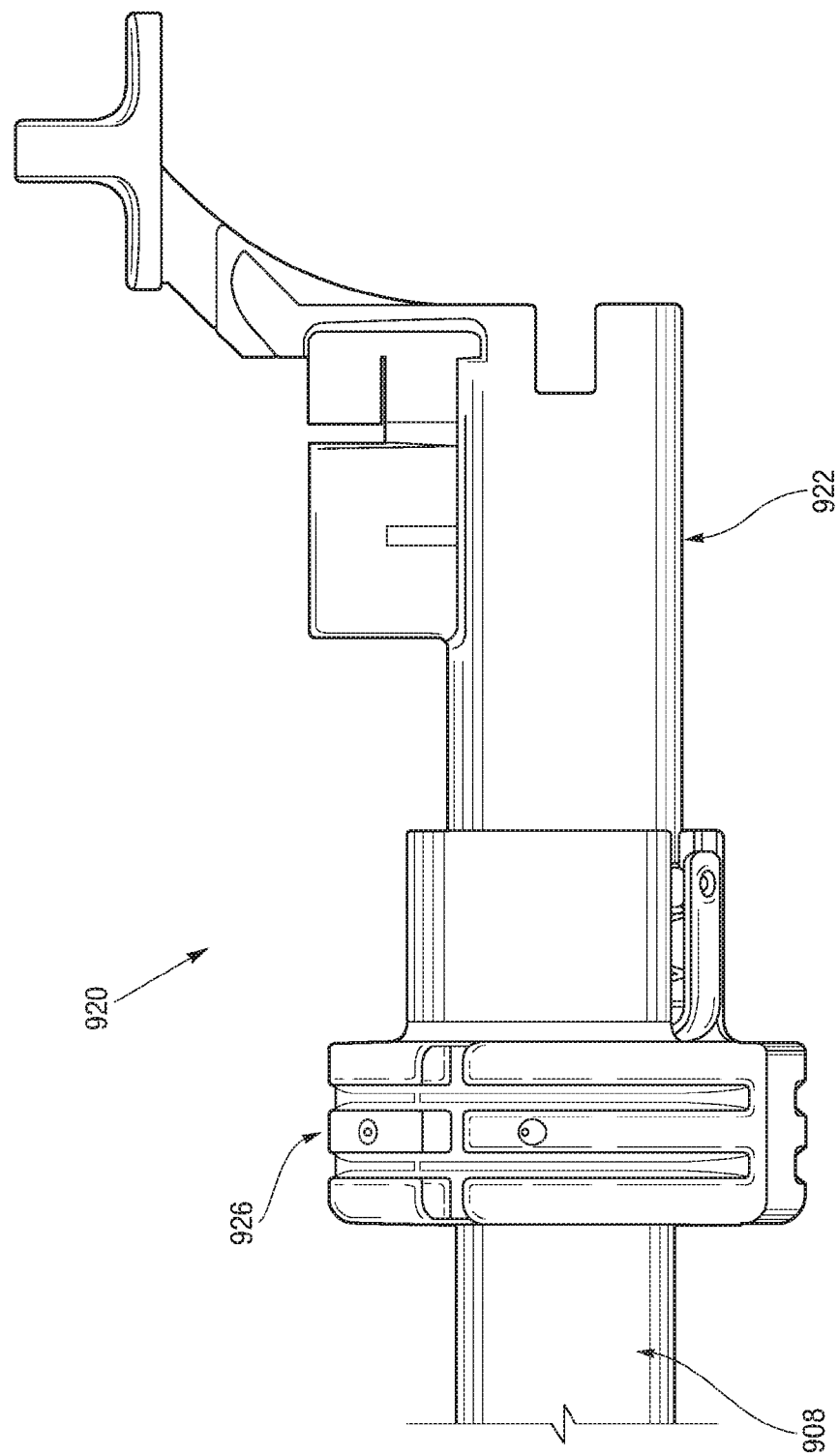

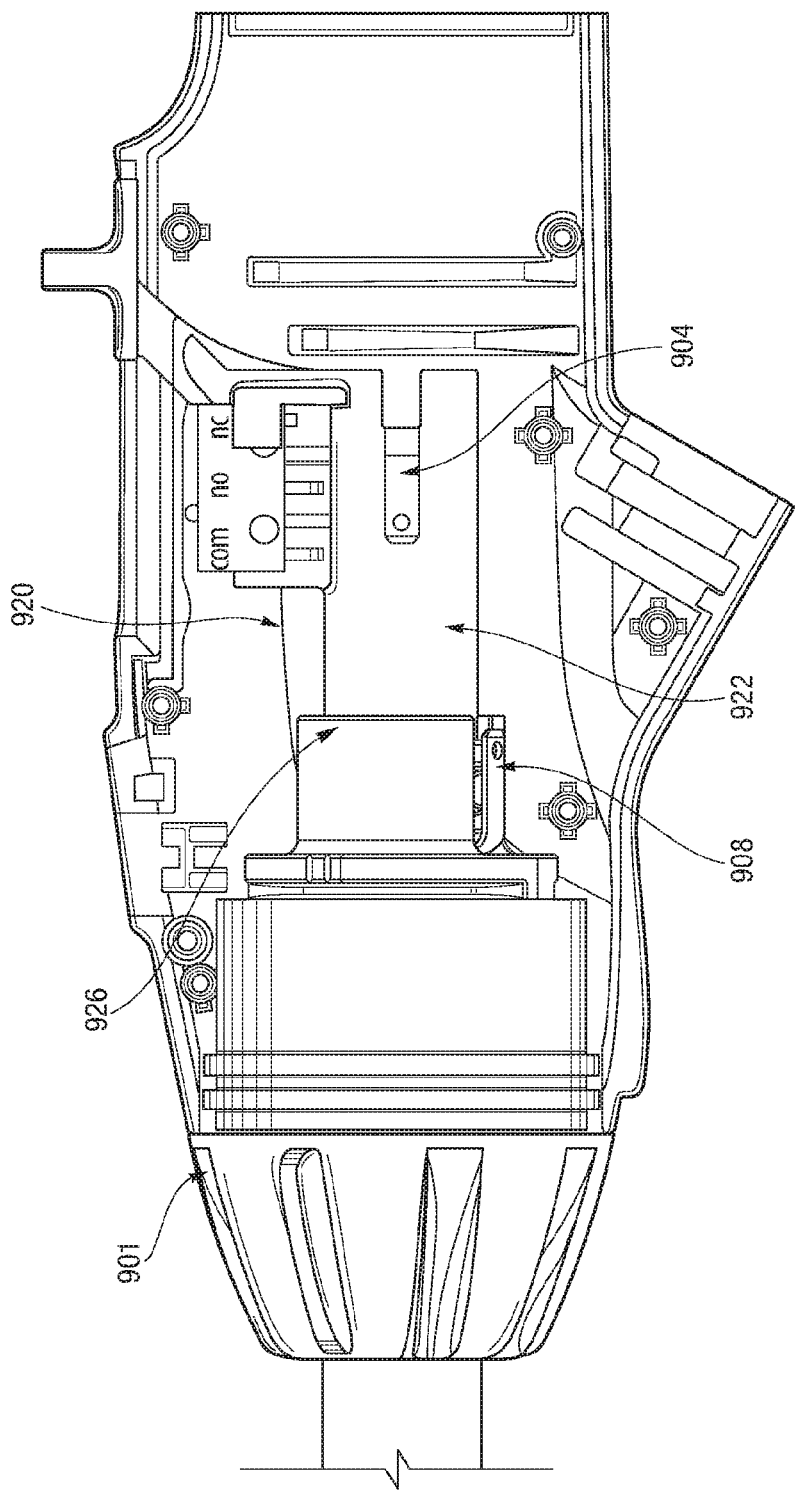

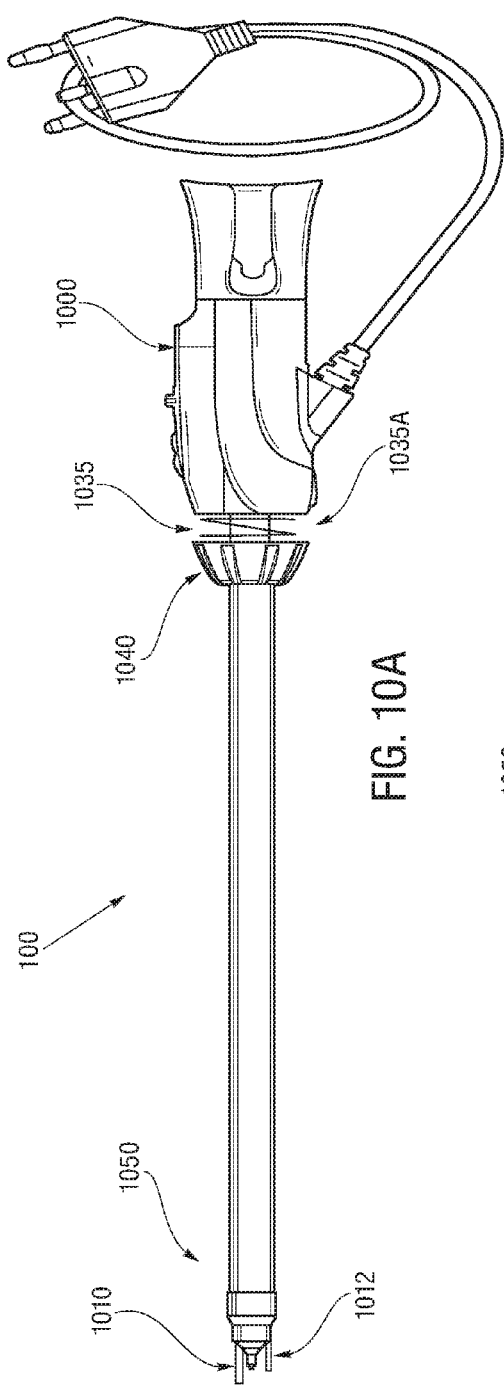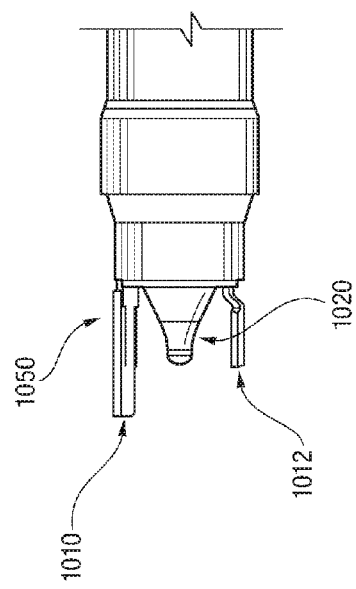
FIG. 10A
FIG. 10B

UNITARY ENDOSCOPIC VESSEL HARVESTING DEVICES WITH AN ELASTIC FORCE

TECHNICAL FIELD

The presently disclosed embodiments relate to endoscopic cannulas and methods of their use.

BACKGROUND

Vessel harvesting is a surgical technique that is commonly used in conjunction with coronary artery bypass surgery. During a bypass surgery, blood is rerouted to bypass blocked arteries to restore and improve blood flow and oxygen to the heart. The blood may be rerouted using a bypass graft, where one end of the by-pass graft is attached to a blood source upstream of the blocked area and the other end is attached downstream of the blocked area, creating a "conduit" channel or new blood flow connection bypassing the blocked area. Commonly, a surgeon will remove or "harvest" healthy blood vessels from another part of the body to create the bypass graft. The success of coronary artery bypass graft surgery may be influenced by the quality of the conduit and how it is handled or treated during the vessel harvest and preparation steps prior to grafting.

Vessel harvesting methods involve selecting a vessel, traditionally, the great saphenous vein in the leg or the radial artery in the arm to be used as a bypass conduit sealing off and cutting smaller blood vessels that branch off the main vessel conduit and harvesting the main conduit from the body. This practice does not harm the remaining blood vessel network, which heals and maintains sufficient blood flow to the extremities, allowing the patient to return to normal function without noticeable effects.

Minimally invasive technique for vessel harvesting is known as endoscopic vessel harvesting, a procedure that requires only small incisions. While the endoscopic vessel harvesting procedure is an improvement over a traditional "open" procedure that required a single, long incision from groin to ankle, the endoscopic procedure is still cumbersome and difficult. In particular, current endoscopic harvesting systems require multiple tools, which increases the potential for injury to the bypass conduit as well as increases the duration of the procedure. Accordingly, improvements in systems and methods for endoscopic vessel harvesting are still needed.

SUMMARY

Unitary endoscopic vessel harvesting devices are disclosed. In some embodiments, such devices comprise an elongated body having a proximal end and a distal end, a tip disposed at the distal end of the elongated body; and a cutting unit having a first cutting portion (i.e. cutting blade or cutting member) and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel, finally a biasing member engaged with the cutting unit to bias at least one cutting portion toward the other cutting portion.

In some embodiments, the present disclosure provides a method for harvesting a blood vessel, the method includes a step of advancing a cannula having a dissection tip disposed at a distal tip of an elongated body along a main vessel to separate the main vessel and its branch vessels from the surrounding tissue. The method further includes a step of moving a first cutting portion and a second cutting portion in a distal direction from a position proximally of the dissection tip to capture a blood vessel between the first and second cutting portions and rotating at least one of the first cutting portion and the second cutting portion circumferentially about the tip toward one another to cut the captured blood vessel via a biasing member engaged with at least one cutting portion toward the other cutting portion.

In some embodiments, the present disclosure provides a system including a surgical device. The surgical device including an elongated body having a proximal end and a distal end and a control collar and a tip disposed at the distal end of the elongated body. The surgical device having a cutting unit having a first cutting portion and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel. The surgical device having a biasing member engaged with the cutting unit to bias at least one cutting portion toward an another cutting portion.

Further features and advantages will become more readily apparent from the following detailed description when taken in conjunction with the accompanying drawings.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 2A-2C illustrate a dissection procedure using an endoscopic cannula of the present disclosure.

FIG. 3A, FIG. 3B and FIG. 3C illustrate an embodiment of a cutting unit of an endoscopic cannula of the present disclosure.

FIGS. 4A-4D illustrates an embodiment of a cutting unit of an endoscopic cannula of the present disclosure.

FIGS. 5A-5B illustrate an embodiment of a dissection tip of the present disclosure.

FIGS. 8A-8B illustrate an embodiment of a cutting unit of an endoscopic cannula of the present disclosure.

FIGS. 9A-9G illustrate an embodiment of a cutting unit of an endoscopic cannula of the present disclosure.

FIGS. 10A-10D illustrate an embodiment of a cutting unit of an endoscopic cannula of the present disclosure.

Figure 1A:
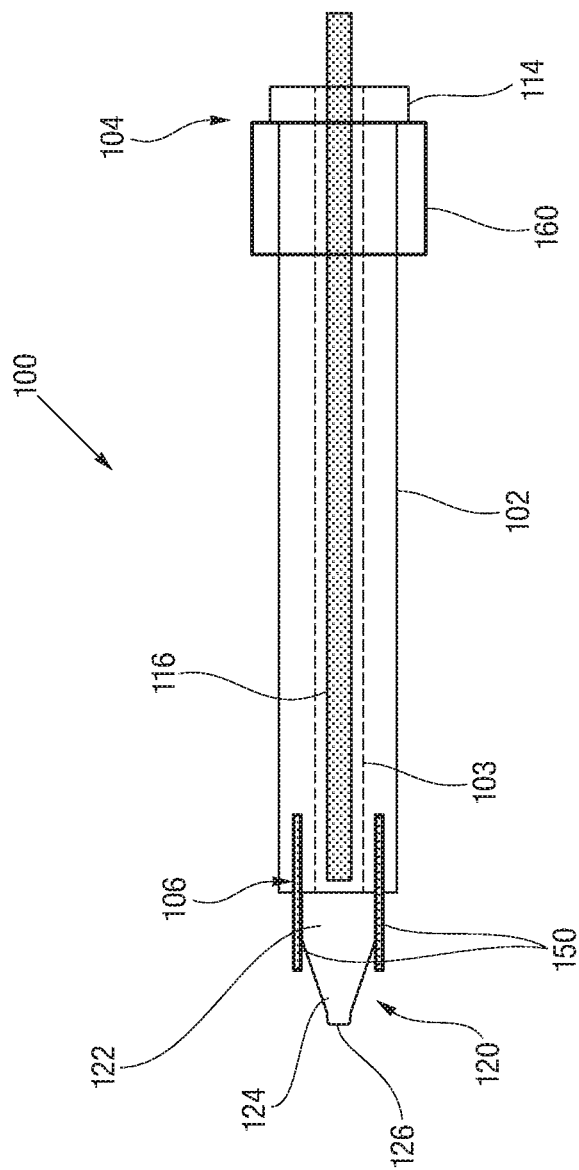
FIG. 1A illustrates a side view of an embodiment of an endoscopic cannula of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

The present disclosure provides a unitary device for endoscopic vessel harvesting. Present systems for endoscopic vessel harvesting contain multiple components. Typically, an endoscopic dissection device is used to isolate the main vessel from the surrounding connective tissue by dissecting the main vessel from surrounding connective tissue. An endoscopic cannula is then used to introduce yet another device, an endoscopic tributary sealing instrument, to seal and sever side branches. Once the side branches are sealed, yet another device is used to harvest a section of the main vessel to be used as a bypass graft. The unitary devices of the present disclosure combine the dissection function, the tributary sealing and severing function, and, optionally, main vessel sealing and severing function, which can result in decreased vessel manipulation and improvement in ease of the procedure. The devices of the present disclosure may also be used to extract the sealed and severed main vessel from the patient.

Decreased vessel manipulation may decrease the potential for injury to the graft. Repeated vessel contact with multiple passes of harvesting instrumentation increases potential vessel injury. A unitary device such as the device of the present disclosure may dissect, i.e., separate the main vessel, from surrounding tissue, cauterize and transect the tributaries and the main vessel as the device is advanced, and the vessel may be harvested with a single passage of the device, rather than multiple device insertions and retractions. Such a device with a decreased diameter may be used for dissection as well as tributary ligation; graft trauma should be decreased. The relative smaller diameter of the present device can also facilitate harvesting of more tortuous vessels; for example, the internal mammary artery.

Referring to FIG. 1A, an endoscopic cannula 100 of the present disclosure includes an elongated body 102 having a proximal end 104 and a distal end 106, terminating with a dissection tip 120. The cannula 100 further includes an cutting unit 150 disposed about the distal end 106 for sealing and cutting a blood vessel and a control handle 160 for controlling the cutting unit 150.

The cutting unit 150 includes an elastic device that provides an elastic force during operation of the cutting unit 150. The elastic device may be external or internal to the endoscopic cannula 100.

In some embodiments, the elongated body 102 is configured for passing extravascularly through an entry incision to a vessel harvesting site. To aid in navigating the elongated body 102 to a site of harvesting, the elongated body 102 may be sufficiently rigid axially along its length. To provide the elongated body 102 with such characteristic, in an embodiment, the elongated body 102 may be made from a biocompatible material, such as, plastic material, elastomeric material, metallic material, shape memory material, composite material or any other materials that has the desired characteristics. To the extent desired, the elongated body 102 may be provided with some flexibility to move radially or laterally from side to side depending on the application.

In some embodiments, the elongated body 102 of the cannula 100 may be solid. In other embodiments, the endoscopic cannula 100 may include one or more lumen with lumena that accommodate advancing instruments or materials therethrough. In some embodiments, the endoscopic cannula 100 may include an endoscopic lumen 103 through which an endoscope 116 may be advanced for visualizing procedures performed using the cannula 100. The endoscopic cannula 100 may include an adapter 114 at the proximal end 104 for advancing the endoscope 116 into the endoscopic cannula 100. Additional lumens of the cannula 100 are described below.

In some embodiments, the endoscopic cannula or cannula 100 may include a dissection tip 120 disposed at or about the distal end 106 of the endoscopic cannula 100. A viewing tip of the endoscope may be positioned inside the dissection tip 120. In some embodiments, the dissection tip 120 may include an inner cavity in fluid communication with the endoscopic lumen 103 to enable the endoscope 116 to be advanced into the dissection tip 120. In some embodiments, a chip-on-a-tip type of an endoscope may be integrated inside the dissection tip 120. The dissection tip 120 may also be transparent to allow for endoscopic viewing through the tip 120 while procedures are performed using the cannula 100. The dissection tip 120 in some embodiments, may be provided with any shape as long as it facilitates endoscopic viewing therethrough, and allows for necessary control during tissue dissecting, i.e. separation. In some embodiments, the dissection tip may be generally conical.

In some embodiments, the dissection tip 120 may include a generally flat shoulder 122, and a tapered section 124 which terminates in blunt end 126 for atraumatic separation of a vessel segment, being harvested from surrounding tissue, while minimizing or preventing tearing or puncturing of nearby vessels or tissue as the endoscopic cannula 100 is navigated along the vessel segment. Although illustrated as being blunt, it should of course be understood that, to the extent desired, the end 126 of the dissection tip 120 may be made relatively pointed to enhance advancement of the cannula 100. Further the generally flat shoulder 122, and the tapered section 124 may be configured differently structurally, so as to enhance the operability of the cannula 100. For example, the generally flat shoulder 122, and the tapered section 124 may be configured to include one or more other elements that assist in the operation and performance of the cutting unit 150.

Figure 1C:
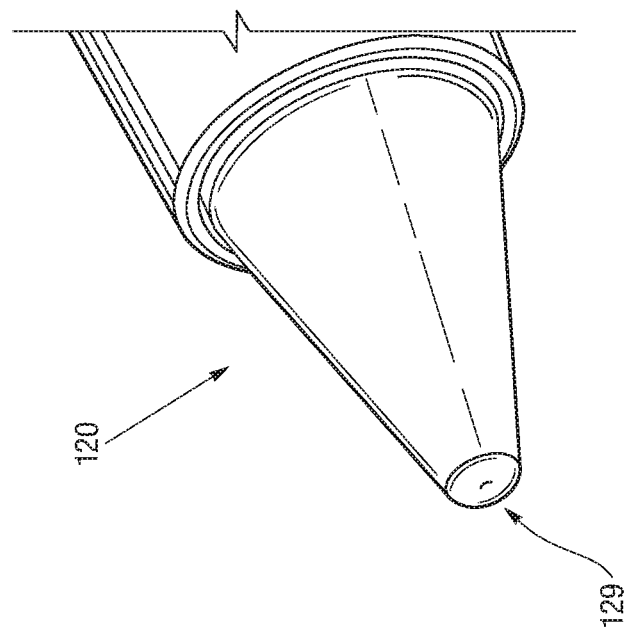
FIG. 1B and FIG. 1C illustrate an embodiment of a dissection tip of the present disclosure having an indent at the distal tip.
Figure 1B:
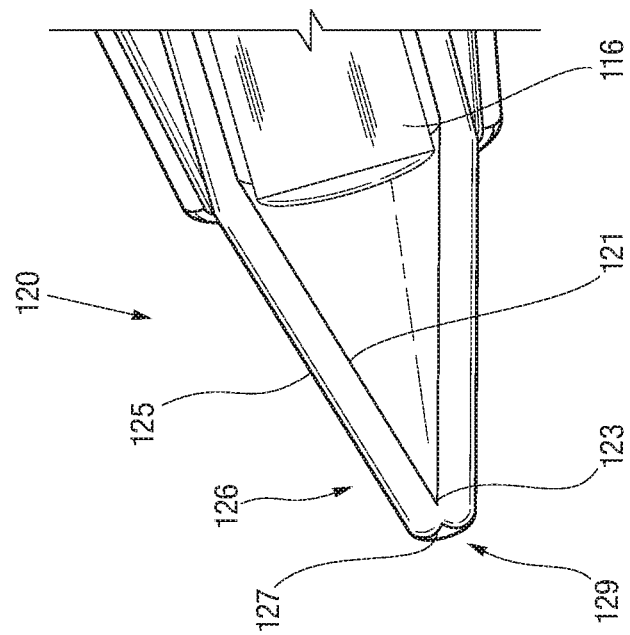

In reference to FIG. 1B and FIG. 1C, in some embodiments, the dissection tip 120 may be cone shaped, and may be shaped at its distal end 129 in a manner so as to minimize the negative effects of visual distortion or blinding at the center of the endoscopic view field when viewing through an endoscope inserted into the cannula 100, with a light source (not shown) and camera system (not shown). Internal surface 121 of the dissection tip 120 may be tapered, with a relatively constant slope toward the distal end 126 of the dissection tip 120, terminating at an internal apex 123, which may be a sharp point, as shown in FIG. 1C. External surface 125 of the dissection tip 120 may also be tapered with a constant slope toward the distal end 126 of the dissection tip 120; however, at the distal end 126, a relatively rounded, blunt end may be formed to minimize tissue damage during dissection. As illustrated, at the distal end 106, the external surface 125 of the dissection tip 120 may be folded back on itself in a proximal direction to then terminate at an external apex 127, maintaining the blunt exterior surface and forming an indent in the distal end of the dissection tip 120. Both the internal apex 123 and the external apex 127 may be collinear with the central longitudinal axis of the cannula 100 and, thus, in some embodiments, the endoscope 116. In other words, the centers of the internal apex 123 and the external apex 127 are located on the central longitudinal axis of the cannula 100. By providing an apex on each of the internal surface 121 and the external surface 125 of the dissection tip 120 that are also collinear with the axis of the endoscope 116, those surfaces perpendicular to the light path (which is parallel to the endoscope axis) may be eliminated, which then may eliminate light refraction from the perpendicular surface back into the camera and, thus, may minimize or eliminate the visual distortion or blinding when viewing through the endoscope 116 with a light source and camera system.

Still referring to FIG. 1B and FIG. 1C, to reduce likelihood of trauma during the dissection process, in some embodiments, the dissection tip 120 may be radially pliable, flexible or deformable so that the dissection tip may deflect slightly under exertion of force applied to the dissection tip 120. In some embodiments, the dissection tip 120 is radially compressible so that the walls of the dissection tip 120 can deform under exertion of force normal to the tip surface. To that end, the dissection tip 120 may be formed from thin wall plastic material to enable the dissection tip to flex under load. Suitable materials include, but are not limited to, polycarbonate, polyethylene terephthalate glycol-modified (PETG), polyethylene terephthalate (PET) and other materials that provide enough optical clarity while allowing the dissection tip to flex under load. At the same time, the dissection tip 120 may be provided with sufficient column strength in axial or longitudinal direction to allow dissection of the vessel from the surrounding connective tissue. Other characteristics of the dissection tip 120 are contemplated, such as having variable strengths: (1) in an axial direction versus a longitudinal direction, wherein the axial strength is greater than the longitudinal strength; (2) in a longitudinal direction versus an axial direction, wherein the longitudinal strength is greater than the axial strength; or (3) the axial direction versus a longitudinal direction, wherein the axial strength is approximate the longitudinal strength. It is also possible that the dissection tip 120 may include two or more materials, wherein at least one material can have different material properties, such as elasticity, hardness, tensile strength.

Figure 2A:
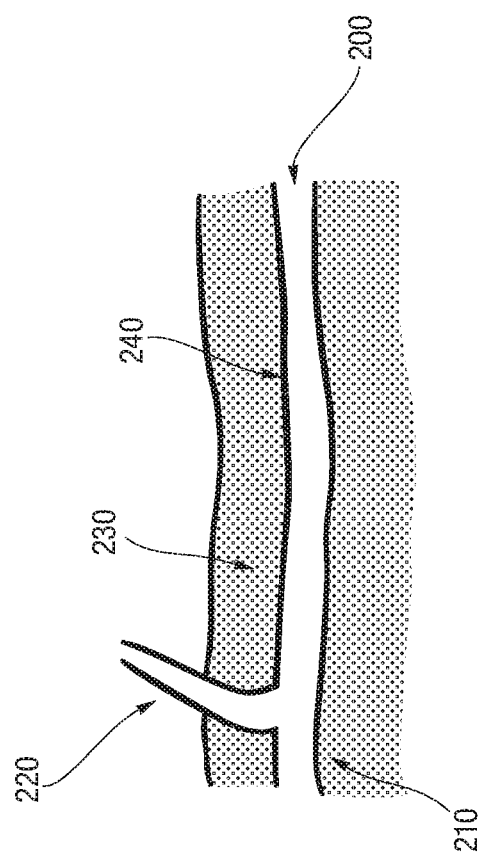
Figure 2B:
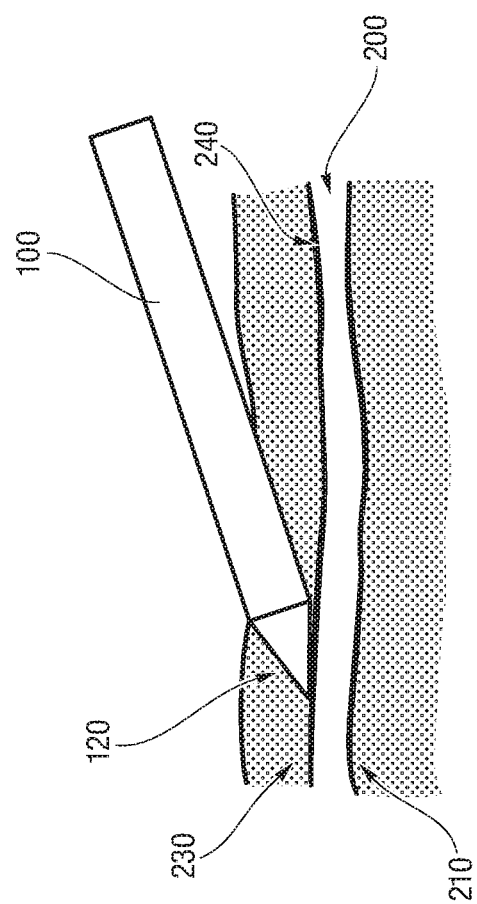

In reference to FIGS. 2A-2C, blood vessels used in bypass grafting (e.g. greater saphenous vein or radial artery), lie in the subcutaneous space, beneath the surface of the skin. The vessel 200 is composed of a main trunk 210, and branch vessels 220 that emanate from the vessel trunk 210, as shown in FIG. 2A. The vessel 200 and its branches 210 are encased in subcutaneous fatty connective tissue 230, and need to be dissected free of the surrounding fatty connective tissue 230 before the main vessel 200 may be harvested. The subcutaneous fat 230 is softer than skin, muscle, fascia or other connective tissues. Although adherent to the vessel 200, the fatty connective tissue 230 forms an interface 240 with the vessel 200 that may be cleanly dissected; that is, there is a natural dissection plane between the outer layer of the vessel 200 (the adventitia), and the surrounding subcutaneous fat 230.

FIG. 2B illustrates dissection of the main trunk 210 of the vessel 200 with the dissection tip 120 along the natural dissection plane, with the dissection tip 120 advanced along the adventitial surface of the vessel 200. Isolation of the vessel 200 from surrounding fatty connective tissue 230 along this plane, typically, does not require high dissection forces. In some embodiments, the dissection tip may 120 be provided with sufficient column strength to dissect the vessel 200 from the surrounding tissue 230 along the natural dissection plane between them.

On the other hand, as is illustrated in FIG. 2C, as the dissection tip 120 approaches a branch vessel 220, the dissection tip 120 may catch the branch vessel 220 at a junction 250 between the branch vessel 220 and the main vessel 200. Application of excessive force with the dissection tip 220 may avulse the branch vessel 220 and sever it from the trunk vessel 210, or may otherwise cause damage to the main vessel 200. To that end, in some embodiments, the dissection tip 120 is provided with sufficient column strength to dissect the vessel 200 from the surrounding tissue 230 along the natural dissection plane between them, while being sufficiently pliable to deform or deflect from the branch vessel 220 with the application of increased force, to decrease the potential of trauma to the graft vessel during dissection around branch vessels. It should of course be understood that the rigidity of the dissection tip 120 may be varied from fully flexible to semi-rigid to rigid, in accordance with requirements of the procedure.

The cannula 100 may further include one or more end-effectors for cauterizing or sealing and cutting a blood vessel, either a branch vessel or the main vessel.

In reference to FIG. 3A, in some embodiments, the cutting unit 150 of the cannula 100 may include a first cutting member 302 and a second cutting member 304, each having a cutting portion 310, 312 extending from their respective distal ends. In some embodiments, as discussed in more detail below, the cutting portions 310, 312 are biased toward one another.

Figure 3C:
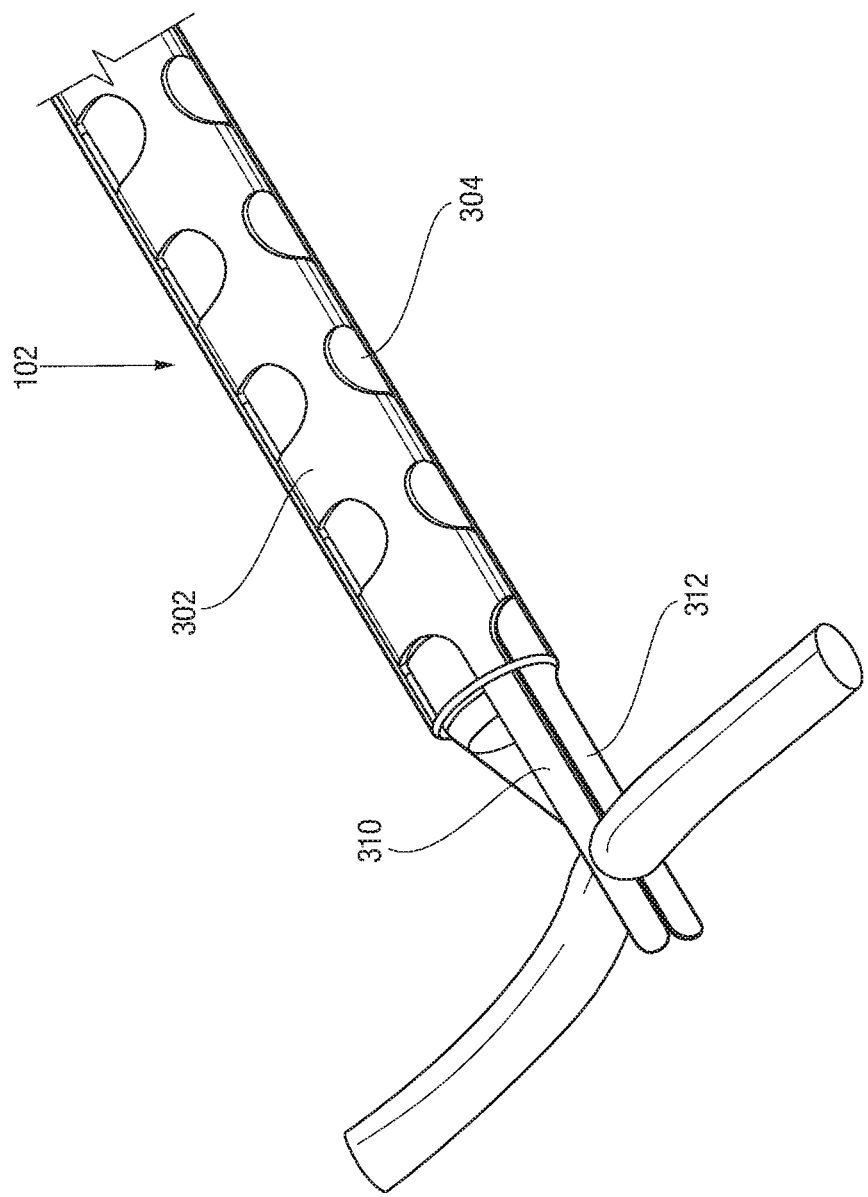

In reference to FIGS. 3A-3C, FIG. 3A shows the cutting unit 150 in its retracted position during dissection. For example, the first cutting member 302 and the second cutting member 304 may be moveable in a longitudinal direction relative to the elongated body 102 of the cannula 100. In this manner, the cutting portions (i.e. cutting blades or cutting members) 310, 312 may be moved from an initial, retracted position during the dissection as in FIG. 3A, in which the cutting portions 310, 312 are retracted substantially proximally of the dissection tip 120 not to interfere with the dissection, to an operational or extended position of FIG. 3B for sealing and cutting, in which the cutting portions 310, 312 may be advanced distally for the user to see the cutting portions and to provide enough capture length for the vessel. In some embodiments, the cutting portions 310, 312 may at least partially extend beyond the dissection tip 120 to capture a blood vessel the cutting portions 310, 312. In addition, in some embodiments, the first cutting member 302 and the second cutting member 304 may be rotatable relative to one another. In this manner, the cutting portions 310, 312 may be moved from an open position when the cutting portions 310, 312 are apart or spaced away from one another to capture a blood vessel therebetween, as shown in FIG. 3B, to a closed position when the cutting portions 310, 312 are brought towards one another around the dissection tip 120 to seal and cut the blood vessel, as shown in FIG. 3C. In some embodiments, the first cutting member 302 and the second cutting member 304 are configured so both cutting portions 310, 312 can be rotated circumferentially about the dissection tip 120 toward one another in both clockwise and counterclockwise direction depending on the location of the blood vessel to be captured between the cutting portions 310, 312. Such bi-directional, circumferential movement of the cutting portions 310, 312 may allow the user to operate on blood vessels on all sides of the cannula 100 to save time and reduce cannula manipulation during the procedure as the user does not need to be concerned about the orientation and position of the cannula 100 in relation to the blood vessel. In addition, it may reduce the potential for the cutting portions to twist the side branches, thereby exerting traction on the blood vessel and consequent damage to the graft. The bi-directional movement may also be more-intuitive to the user and eliminates the need to remember which side is the active side for cautery and cutting. In other embodiments, one of the cutting portions 310, 312 may be stationary and the other one may rotate in both clockwise and counterclockwise toward the stationary cutting portion for easier manipulation and visualization of the cutting portions 310, 312. Of course, the stationary cutting portion may also be moved to a desired orientation by moving the cannula 100.

Still referring to FIG. 3A, FIG. 3B and FIG. 3C, the cutting portions (i.e. cutting blades or cutting members) of the cutting members 302, 304 may generally be elliptical or blade-like with a rounded distal tip, but any other shape that enables the cutting and sealing of a blood vessel may also be used. To facilitate sealing of the blood vessel, one or both of the cutting portions 310, 312 may be energized, when needed, using various sources of energy, including, but not limited to, resistive heating, ultrasound heating, and bipolar or monopolar RF energy. In some embodiments, the electrodes can be controlled independently of one another. In some embodiments, the cutting portions 310, 312 may be made from a material such as metal that would enable the cutting portions 310, 312 themselves to be energized. Additionally or alternatively, energizing elements, such as metal wires, may be disposed on the cutting portions 310, 312. When energized, the energizing elements may be brought in contact with the blood vessel by the cutting portions 310, 312 to seal the blood vessel. In some embodiments, one or both of the cutting members 310, 312 may include protrusions for use as spot cautery. In some embodiments, one or both of the cutting members 310, 312 may have a sharpened, thin edge for concentrated application of energy to the blood vessel. Such concentrated energy application may require less energy to be applied to the side branch, thereby minimizing extension of cauterizing energy from the side branch towards the main trunk of the blood vessel, and thus eliminating potential trauma to the blood vessel.

Still referring to FIG. 3A, FIG. 3B and FIG. 3C, to facilitate cutting of the blood vessel subsequent to sealing of the blood vessel, in some embodiments, one of the opposing edges of the cutting portions 310, 312 between which cutting occurs may have a leveled face while the other one may be a sharpened, thin or pointed so that the tissue is not cut in a scissor-like motion but with a thin edge against a flat surface. To that end, in some embodiments, both edges of the cutting members 310 may be sharpened edges, while both edges of the cutting portion 312 may be flat, or vise versa. Alternatively, the cutting portions 310, 312 may have one sharp edge or blade edge and one flat edge with the sharp edge of one cutting portion facing the flat edge of the other cutting portion. It should be noted that in some embodiments, the blood vessel may be both sealed and cut using energy, as described above. It should of course be understood that, in some embodiments, the opposing edges the opposing edges of the cutting portions 310, 312 may both be sharpened so the tissue is cut in a scissor-like manner.

As shown in FIG. 3B and FIG. 3C, in some embodiments, the cutting members 302, 304 may be substantially u-shaped and disposed in the same plane relative to the cannula body 102. In some embodiments, the cutting members 302, 304 may include respective cutouts and fingers 314, 316 along the edges to enable circumferential movement of the cutting members 302, 304 relative to one another as shown in FIG. 3B.

Figure 4A:
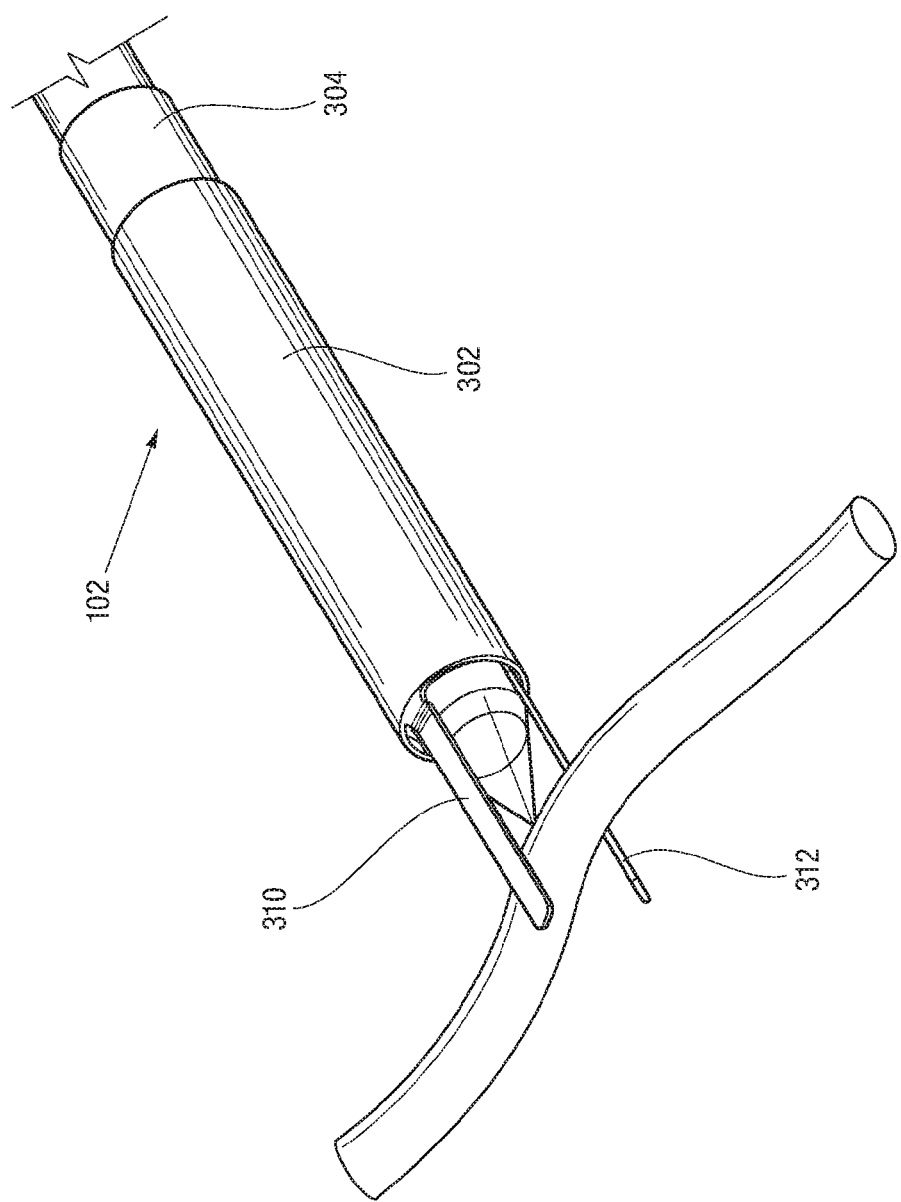

In reference to FIG. 4A and FIG. 4B, in some embodiments, the cutting members 302, 304 may be substantially tubular and be disposed in different planes of the cannula body 102. As shown in FIG. 4A, in some embodiments, the cutting member 304 may be concentrically disposed inside within the cutting member 302. Referring to FIG. 4B, in some embodiments, the elongated body 102 of the cannula 100 may be constructed of a series of coaxial tubes, both metal and plastic, that may act as the structural main shaft, the electrical conductive and insulative paths, and the end-effectors, i.e. cutting portions (i.e. cutting blades or cutting members). In some embodiments, there may be three plastic sheaths acting as electrical insulators and mechanical bearing surfaces sandwiched in between two metal conductive tubes for the entire length of the device. The innermost layer may be the inner sheath 402 (plastic) defining an internal lumen 403. The inner sheath 402 may be followed outwardly by the inner electrode tube 404 (metal), middle sheath 406 (plastic), outer electrode tube 408 (metal) and outer sheath 410 (plastic), and finally a shrink jacket 412. In some embodiments, instead of three plastic sheaths, the electrical insulation may be provided using non-conductive coatings or similar means. For example, in some embodiments, the electrodes 404, 408 may be coated with polyvinyldyne fluoride (PVDF), but other non-conductive coating may also be used.

The inner electrode tube 404 may be used to form the first cutting member 302 and the outer electrode tube 408 may be used to form the second cutting member 304, with the cutting portions 310, 312 being formed at the distal ends of the inner electrode tube 404 and the outer electrode tube 408. To enable the cutting portions 310, 312 to capture, seal and cut blood vessels, the inner electrode tube 404 and the outer electrode tube 408 may be slidable in the longitudinal direction relative to the cannula 100 and rotatable relative to one another. Further, because the cutting portions 310, 312 are formed from the inner electrode tube 404 and the outer electrode tube 408, the cutting portions 310, 312 can be easily energized through the inner electrode 404 and the outer electrode 408. In some embodiments, the cutting portion formed from the inner electrode tube 404 (i.e. inner cutting portion 411) may be bent out of the plane of the inner electrode 404 to enable it to rotate along the same axis and be co-radial with the cutting portion formed in the outer electrode 408 (i.e. outer cutting portion 413 of FIG. 4D). In some embodiments, FIG. 4D shows the inner cutting portion 411 may have a flat face 416 on either side of the inner cutting portion, while the outer cutting portion 413 may have a sharpened or blade edge 418 on both sides, or vice versa. In other embodiments, as described above, each cutting portion 411, 413 may have one sharpened edge and one flat edge, with the flat edge of one cutting portion facing the sharpened edge of the other cutting portion.

Figure 4C:
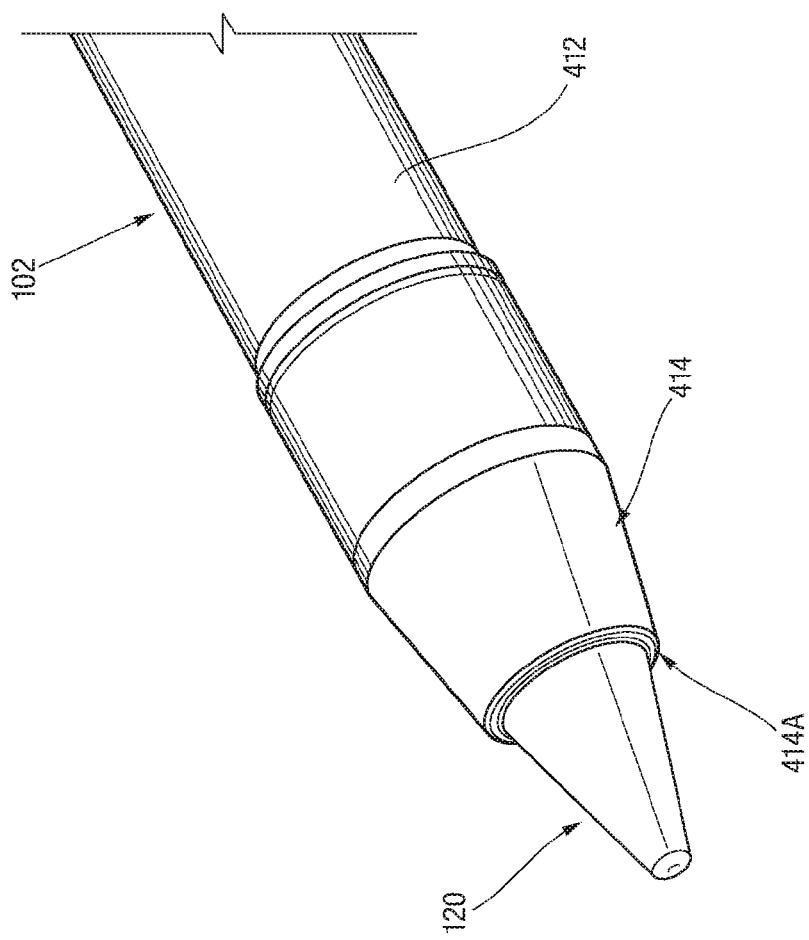

In reference to FIG. 4C, in some embodiments, the dissection tip 120 may be connected to the inner sheath 402 to enable the advancement of the endoscope 116 into the dissection tip though the internal lumen 403. A soft transition element 414 may be used to protect tissue from damage during dissection by smoothing the geometry between the dissection tip 120 and the cannula body 102. The distal end 414A of the transition element 414 may be left unattached to the dissection tip 120 to allow the cutting portions 312, 314 to be advanced distally through the transition element 414, as shown in FIG. 4D. In some embodiments, the transition element 414 may be made of a flexible material so during dissection, the transition element 414 would comply with the dissection tip creating a smooth transition and also a tight seal to prevent tissue or bodily fluids from entering the cannula 100. On the other hand, a flexible sleeve would be able to deflect and expand to allow the cutting portions 312, 314 to be advanced out distally though the transition element 414. In some embodiments, the surface of the sleeve may be coated with a lubricious substance to make the extension of the cutting portions 312, 314 through the transition element 414 easier and smoother by decreasing friction between the cutting portions 312, 314 and the transition element 414. FIG. 4C illustrates that a thin-walled shrink tube 412 may be placed over the outer surface of the cannula body for aesthetic purposes and to assist in securing the transition.

In reference to FIGS. 5A and 5B, in some embodiments, the dissection tip 120 may include a transition element 514 made from a stiff material. The transition element 514 may be configured with an opening or cut out 512 that may allow for the two cutting portions 310, 312 to extend out of the transition element 514 (FIG. 5B) and cannula 100 and retract into the main cannula 100 (FIG. 5A). The transition element 514 can be connected to the cannula 100 of the main device and also rests over the dissection tip 120. In some embodiments, the dissection tip 120 and the transition element 514 may be integral. In some embodiments, they can be provided as separate parts.

The profile of the transition element 514 may create a gradual decrease in diameter toward the distal end. The transition element 514 can be constructed of a strong and stiff material that maintains its geometry throughout dissection to reduce the dissection load. During the procedure, due to its stiffness, the transition element 514 may maintain its form and support the tissue sliding over the transition element 514. Suitable materials for the transition element include, but are not limited, to medical grade metals and hard plastics.

Still referring to FIGS. 5A and 5B, the length of the cut out 512 may control the extent of rotation of the cutting portions with respect to the dissection tip 120. In some embodiments, the allowable arc of rotation of the cutting portions may be less than a full rotation, depending on the opening of the cut out 512. The cutting portions can have single-sided features, that is, the sharp, conductive edge and a flat conductive edge (i.e. anvil) may be situated on the inside edges of the respective cutting portions, but not on the outside edges.

Figure 6A:
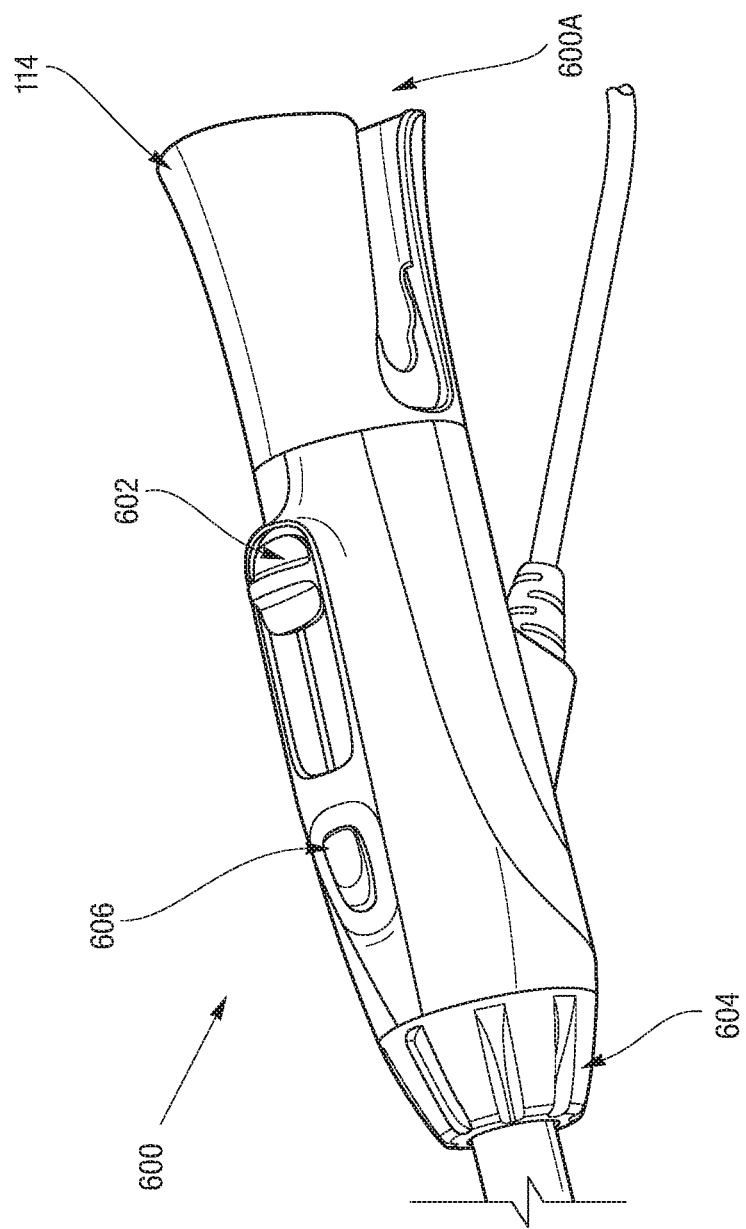
FIG. 6A illustrates an embodiment of a control handle suitable for use with an endoscopic cannula of the present disclosure.
Figure 6C:
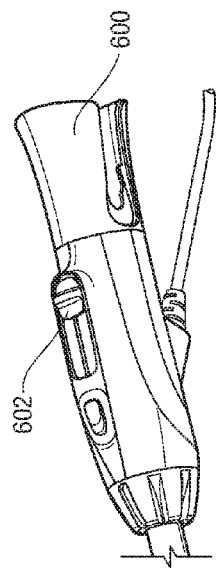
FIGS. 6B-6G illustrate an embodiment of an endoscopic cannula of the present disclosure in operation being controlled by the control handle of FIG. 5.

In reference to FIG. 6A, a control handle 600 may be provided at the proximal end of the cannula 100 for controlling the cutting members. In some embodiments, the control handle 600 may include a translation control 602 for advancing and retracting the cutting members. The control handle 600 can further include a rotation control collar 604 for rotating the cutting members with respect to one another. The control handle 600 can also include an energy control 606 for supplying energy (such as bipolar radiofrequency (RF) energy) to the cutting portions of the cutting members. In some embodiments, an adapter 114 may be located at the proximal end 600A of the control handle 600 for advancing an endoscope into the cannula.

The operations of the device may be described in reference to FIGS. 6A-6G. In operation, an initial incision may be made in conventional manner to expose the target vessel (e.g., the saphenous vein). The cannula 601 (FIG. 7B) may be inserted into the incision and guided to the target vessel. In some embodiments, the cannula 601 may include a smooth tubular sheath around the elongated body for sealing the cannula 601 within the port through which the cannula 601 is introduced into the patient. The cannula 100 may then be advanced substantially along the target vessel to dissect the target vessel from the surrounding tissue. In some embodiments, the cannula 601 may be introduced through a sealable port used to seal the incision to allow insufflation of the space created by the dissection of the target vessel from surrounding tissues.

Figure 6E:
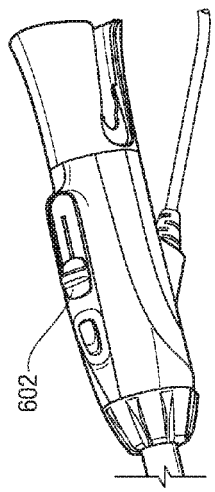
Figure 6G:
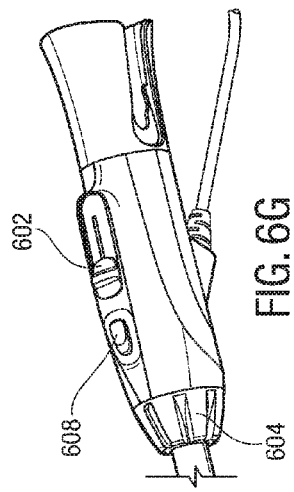
Figure 6B:
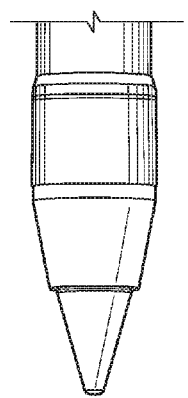
Figure 6D:
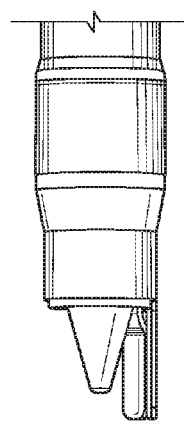
Figure 6F:
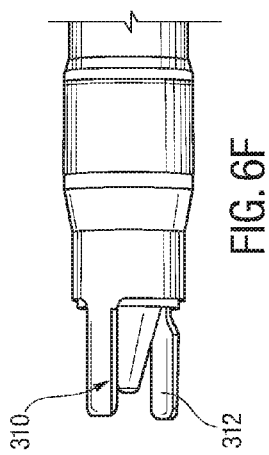

As the cannula 100 is being advanced, the cutting portions of the cutting elements may be kept in a retracted position proximally of the dissection tip so not to interfere with tissue dissection until a branch vessel is encountered, as shown in FIGS. 6B-6G. When a branch vessel is reached, the cutting portions 310, 312 may be moved in a distal direction beyond the dissection tip 120 by advancing the translational control or slider control 602 on the handle 600 distally, as shown in FIGS. 6D-6E. As noted above, the cutting portions may be biased toward one another and may be advanced out together and enter into the field of view of the endoscope in the dissection tip.

Next, the cutting portions may be rotated away from one another using the rotation control 604 to an open configuration, for sealing and cutting the branch vessel. The cutting portions may be rotated around the dissection tip in a circular arc motion. The endoscopic cannula may be positioned such that the target branch vessel may lay across one of the cutting portions regardless of orientation of the branch vessel in relation to the main blood vessel to be harvested. The endoscopic cannula may be designed such that the user can place the endoscopic cannula and the cutting portions as far away from the target main vessel as possible to avoid injury to the main vessel. Next, when the branch vessel is positioned in between the cutting portions 310, 312 the user may allow the cutting portions to come back together into a closed configuration, capturing the branch vessel between them. In some embodiments, the user may bring the cutting portions together manually. Alternatively or additionally, the rotational control may be spring loaded to bias the cutting sections toward one another. The energy control 608 button may then be pressed to transfer the energy into the branch vessel to seal the vessel. In some embodiments, the cutting portions may be energized before the cutting portions make contact with the branch vessel. After sealing is complete and the energy control button 608 is released, the user may continue to advance the rotation control 604 until the cutting portions transect the branch vessel. Once the branch vessel is cut, the user may then retract the cutting portions with the translation control 602 and advance the device to the next branch vessel until all tributaries have been successfully ligated and transected.

In some embodiments, to bias the cutting portions, the control handle 600 may include a biasing member 605 for spring loading the torsional movement of the control collar 604. In various embodiments, both cutting portions may be rotatable, while in other embodiments, only one of the cutting portions may be rotatable and the other one stationary. For example, the cannula 100 can be structured and arranged for externally spring loading the torsional movement between the control handle 600 and the control collar 604 so the cutting portions are kept in a closed configuration. In order to position the cutting portions onto a venous tributary, the control collar 604 can be rotated to move, one or both, cutting portions away from one another into an open configuration. Upon release of the control collar 604, a predetermined amount of compressive force can be applied to the tributary, followed by activation of the bipolar RF energy to cauterize the tributary. The compressive force on the tributary can be achieved by a spring force selection on the control collar 604 to optimize the process of tributary sealing. After application of bipolar cautery to seal the tributary, the cannula 100 can be rotated and/or displaced axially to cut the tributary.

Figure 7A:
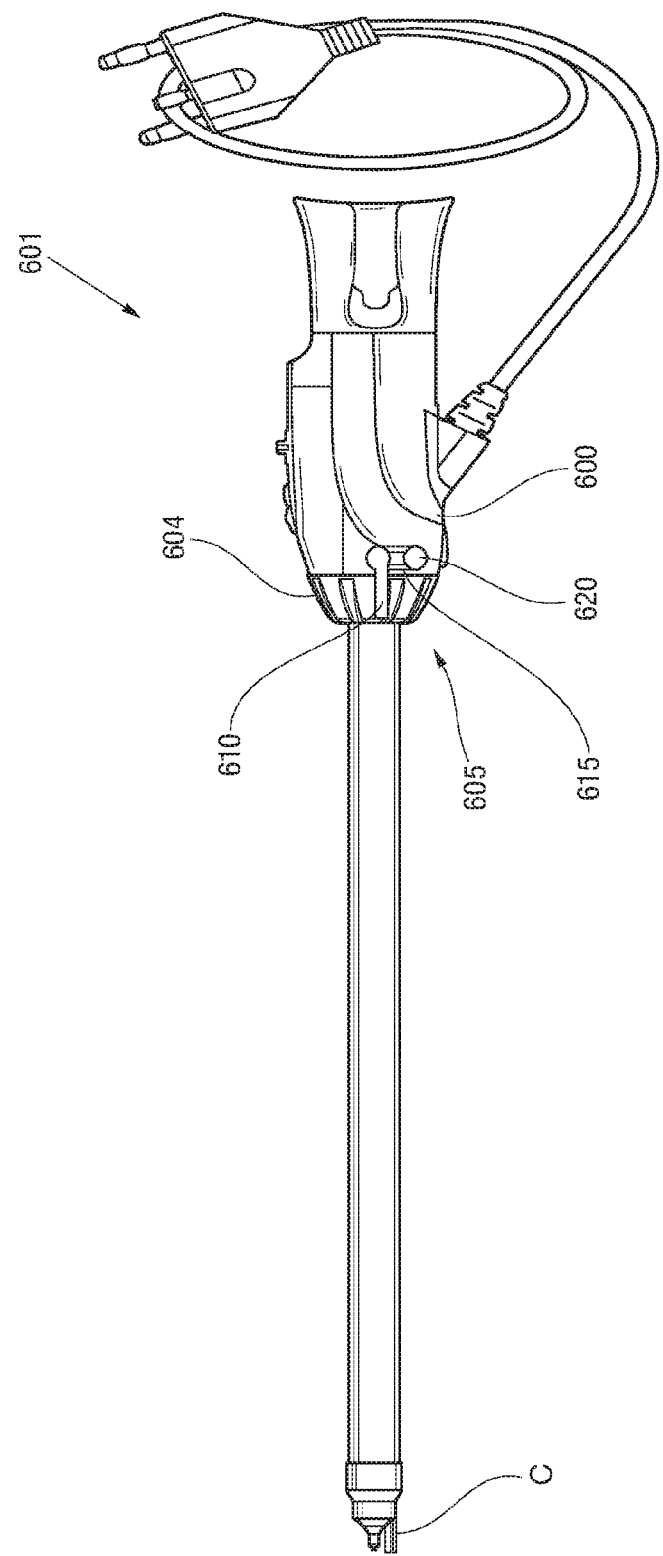
FIGS. 7A-7F illustrate an embodiment of a cutting unit of an endoscopic cannula of the present disclosure.
Figure 7B:
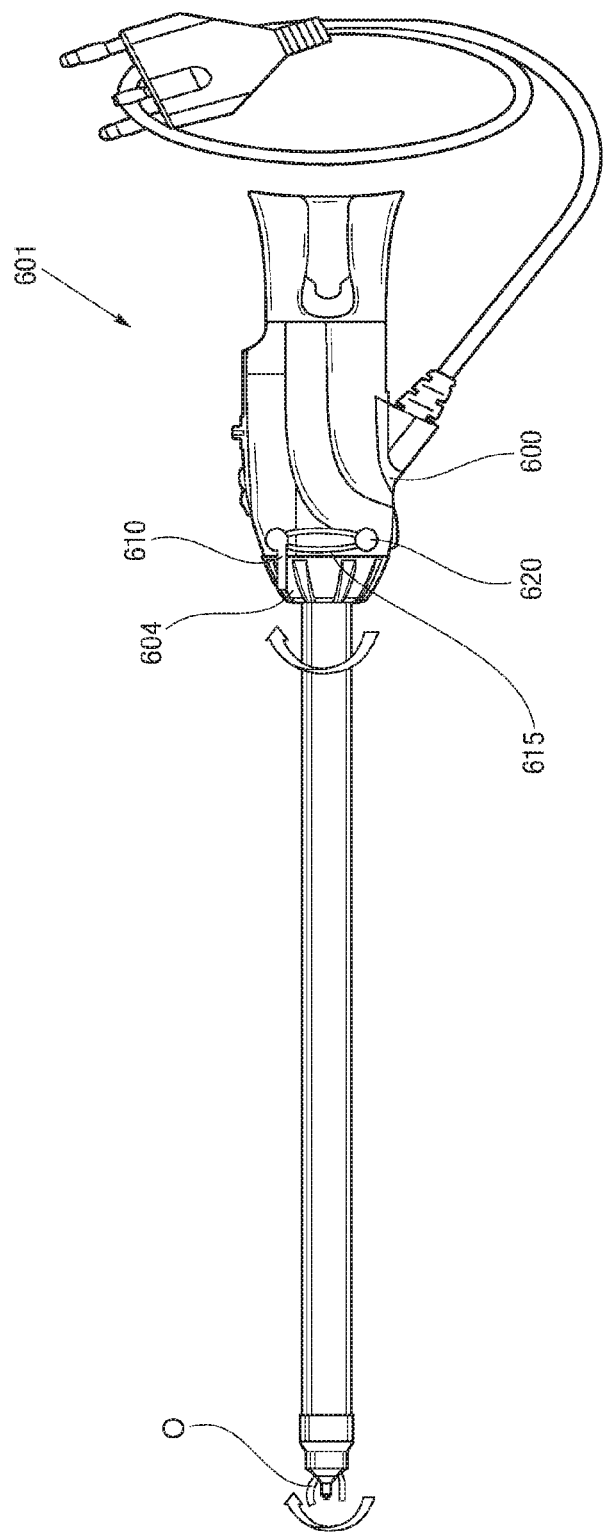

In references to FIGS. 7A and 7B, in some embodiments, the biasing member 605 may include a first control lever 610 attached to an outside surface of the control collar 604 and a corresponding second control lever 620 attached to an outside surface of the control handle 600 of the cannula 100. An elastic device or elastic band 615 may be used to connect the control levers 610, 620, placing the two in compression and likewise exerting a compressive force between the cutting portions to keep the cutting portions are in a closed configuration.

Figure 7D:
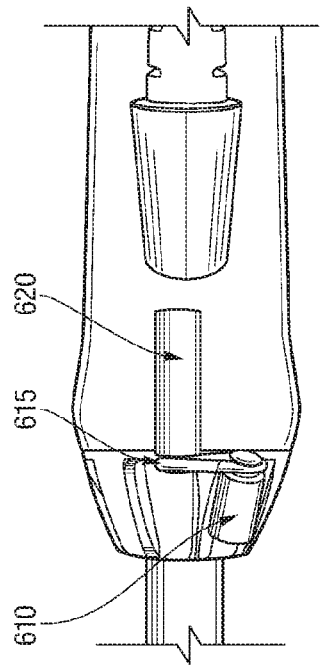
Figure 7F:
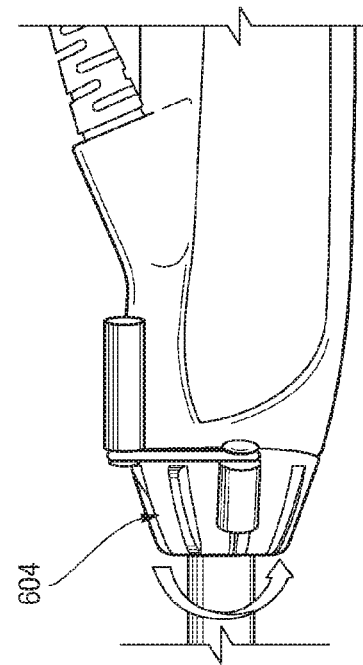
Figure 7C:
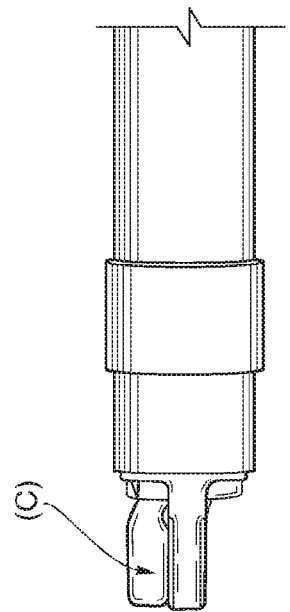
Figure 7E:
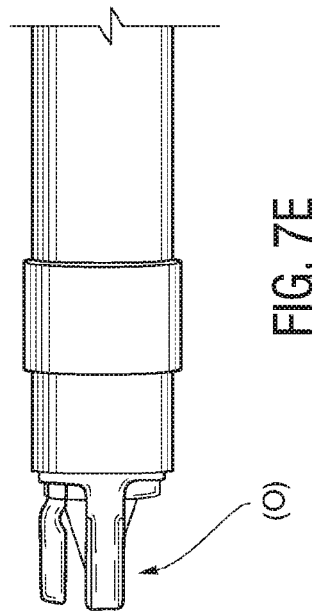

In reference to FIGS. 7C and 7D, the elastic band 615 is in a relaxed or contracted configuration, keeping the cutting portions in a closed configuration. In reference to FIGS. 7E and 7F, moving the rotational control 604 stretches the elastic band 615 and moves the cutting portions into the open configuration. Releasing of the collar may allow the elastic band to contract and move the cutting portions back into the closed configuration.

In some embodiments, the biasing member may be disposed inside the cavity of the control handle and the control collar. In some embodiments, the biasing member 615 may be used to standardize the compressive force applied to branch vessels during the cautery and transection process. In this manner, the variation in manual compressive forces exerted by different clinicians/users during the harvesting procedure may be eliminated to increase the likelihood of achieving hemostasis, thereby avoiding any potential of hemorrhage or bleeding during the procedure. External and internal biased cutting portions may remove the need for the user to maintain his or her hands in opposite directions for the duration of the cautery process so the user may be substantially less tired when performing multiple procedures.

In some embodiments, the cutting portions 310, 312 may also be moveable in a longitudinal direction relative to one another, which may increase a cutting action achieved during transection of branch vessels, as shown in FIGS. 8A and 8B. As shown in FIG. 8A, the cutting portions 310, 312 may be extended distally along the dissection tip together. Then, as shown in FIG. 8B, the user may continue to translate one of the cutting portions 310, 312 distally from the extended position to a "hyper-extended" position. In the hyper-extended position, one of the cutting portions 310, 312 may be advanced further than the other cutting portion in a distal direction. During the surgical process it may be difficult for the cutting portions to transect or cut large diameter venous tributaries following their cauterization. Upon the application of bipolar cautery energy to the tributary, the tributary tissue may be desiccated, transforming it into a toughened fibrous strand, rather than the soft, tubular structure it assumes in its native state. The relative translational movement between the cutting portions may create a "slicing" action, which may help to server even the hardened vessels.

Figure 9A:
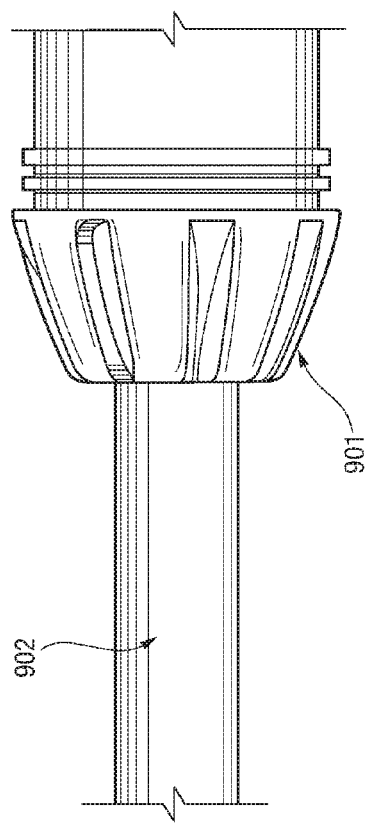
Figure 9B:
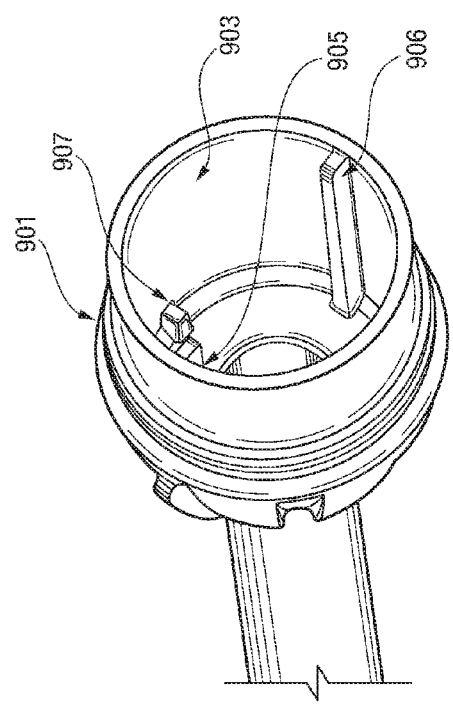

By way of a non-limiting example, FIGS. 9A-9G illustrates an exemplary assembly that can permit movement of the cutting portions in a longitudinal direction relative to one another. In reference to FIG. 9A, a rotator subassembly 901 may be attached at a proximal end of the outer sheath 902. As shown in FIG. 9B, the inner compartment 903 of the rotator subassembly 901 may include two keys 905, 906 and a stop 907, the purpose of which is described below. FIG. 9C illustrates an embodiment of an outer electrode sub-assembly 920, which may be disposed at a proximal end of the outer electrode 908. The outer electrode sub-assembly 920 may include an inner adapter 922 connected to the outer electrode 908 via a compressible element 924. The inner electrode 904 may extend through the outer electrode 908 and into the inner adapter 922, and may be secured to the inner adapter 922. In addition, as shown in FIG. 9D, an outer adapter 926 may be disposed about the outer electrode 908. The outer adapter 926 may be designed to allow the inner adapter 922 to rotate relative to the outer electrode 908, thus rotating the inner electrode 904 in relation to the outer electrode 908. As shown in FIG. 9E, the outer electrode sub-assembly 920 may be inserted into the rotator assembly 901 and a handle 928 is placed around the outer electrode sub-assembly 920.

Figure 9F:
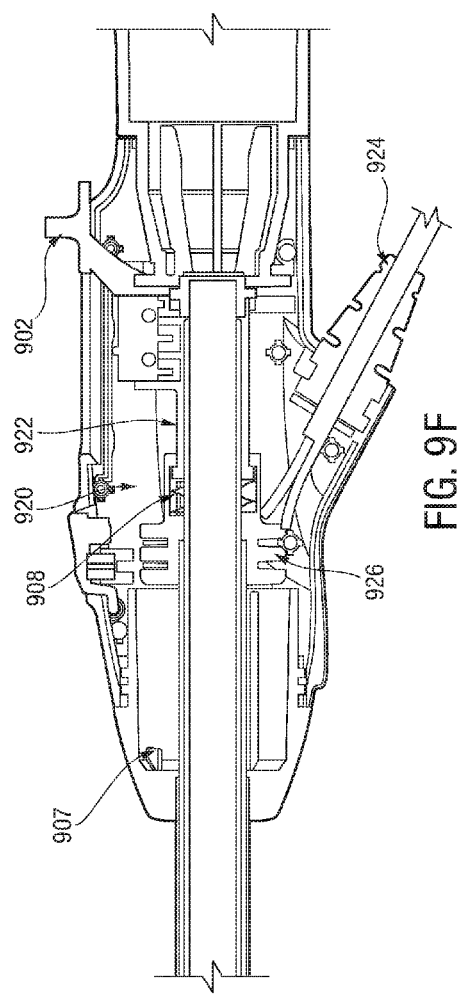
Figure 9G:
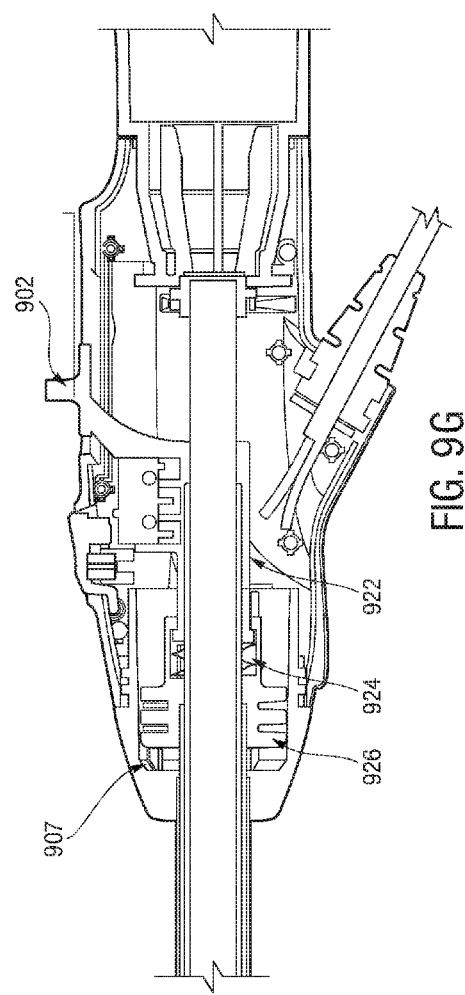

In operation, as shown in FIG. 9F, the outer electrode subassembly 920 may be retracted to retract the cutting portions. To extend the cutting portions, the slider 602 may be advanced in the distal direction to move the outer electrode subassembly 920 in the distal direction. As shown in FIG. 9G, the outer electrode subassembly may be advanced forward until the outer adapter 926 is pressed against the stop 907 of the rotator subassembly 901. At this point, the cutting portions are advanced to an extended position together, as shown for example in FIG. 8A. Next, the slider 902 may be moved further in the distal direction to move the inner adapter 922 to compress the compressible element 924. Such movement of the inner adapter 922 may also move the inner electrode further in the distal direction, while the outer electrode 908 may remain stationary. In this manner, the cutting portion of the inner electrode 904 may be moved in the longitudinal direction relative to the cutting portion of the outer electrode 908 to the hyper-extended position, as shown in FIG. 8B.

In reference to FIG. 10A and FIG. 10B, another embodiment for longitudinally moving the cutting portions relative to one another is illustrated. It should of course be understood that the design shown in FIGS. 9A-9G may be combined with the design of FIGS. 10A-10B. In reference to FIG. 10A, the cannula 100 may include a compressible element or compression spring 1035 positioned in a gap 1035A separating the control collar 1004 from the control handle 1000. An aspect of this configuration may provide for an axial motion between the cutting portions. For example, at least one rotating cutting portion 1010 can be activated by the control collar 1004 and lengthened by approximately 3-5 mm, the control collar 1004 can be displaced forward of the control handle 1000, and the compressible element 1035 placed in the gap 1035A between the control collar 1004 and the control handle 1000, such that retraction of the control collar 1004 against the control handle 1000 results in a 3-5 mm axial excursion of the rotating cutting portion 1010 against the stationary blade 1012.

Figure 10C:
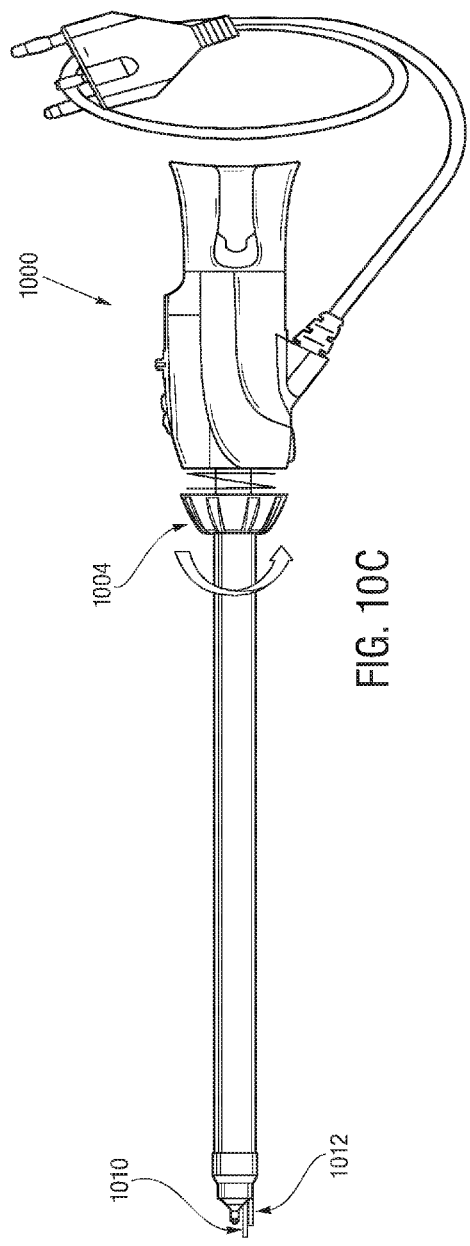
Figure 10D:
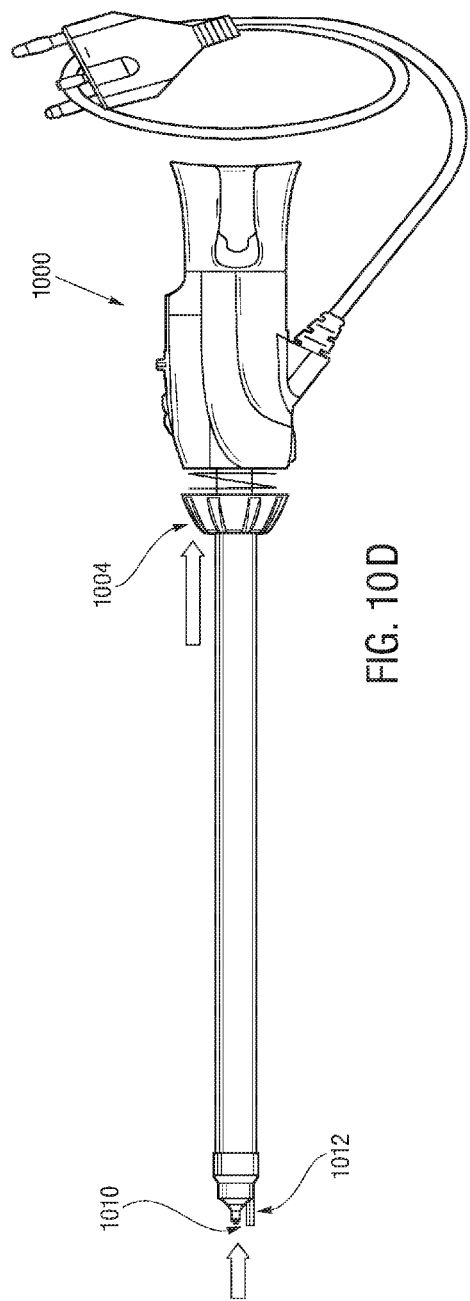

FIG. 10C and FIG. 10D illustrate the use of the axial motion between the two cutting portions 1010, 1012. For example, the control collar 1004 is rotated to close the long rotational portion 1010 onto the stationary cutting portion 1012, and bipolar electro cautery is applied to seal the tributary (FIG. 10C). While maintaining the cutting portions 1010, 1012 in a closed, compressed configuration, the control collar 1004 may be pulled back against the control handle 1000 to retract the long rotational cutting portion 1010 against the stationary cutting portion 1012, providing relative longitudinal movement between the two cutting portions 1010, 1012 (FIG. 10D).

It should be noted while preferred types of energy for various electrodes are indicated in the present disclosure, all electrodes can be energized using various sources of energy, including, but not limited to, resistive heating, ultrasound heating, and bipolar or monopolar RF energy. In some embodiments, the electrodes can be controlled independently of one another. It should also be noted that, when appropriate, the electrodes may be insulated with an insulating coating or insulating sheath.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A surgical device comprising:
an elongated body having a proximal end and a distal end;
a conical tip disposed at the distal end of the elongated body; and
a cutting unit having a first cutting portion and a second cutting portion, the first cutting portion and the second cutting portion being moveable in a longitudinal direction relative to the elongated body from a first position substantially proximal of the conical tip to a second position distal of the conical tip to capture a blood vessel between the first cutting portion and the second cutting portion, at least one of the first or second cutting portions being rotatable relative to another of the first or second cutting portions circumferentially about the tip to cut the captured blood vessel and being biased toward the other of the first or second cutting portions, wherein the first cutting portion has a sharpened edge and an edge of the second cutting portion facing the sharpened edge of the first cutting portion is flat.

2. The surgical device of claim 1 further comprising a biasing member configured to move the cutting portions from an open position where the first and second cutting portions are spaced away from one another to a closed position where the first and second cutting portions are in contact with one another.

3. The surgical device of claim 2 wherein a rotation control collar is disposed at the proximal end of the elongated body for moving the first and second cutting portions from the closed position to the open position, and the biasing member is coupled to the rotation control collar to return the cutting portions to the closed position.

4. The surgical device of claim 1, wherein the first cutting portion and the second cutting are configured to be energized for sealing, cutting or both of the captured blood vessel.

5. The surgical device of claim 1, wherein the at least one of the first or second cutting portions that is rotatable is the second cutting portion and the other of the first or second cutting portions is the first cutting portion, wherein the first cutting portion is stationary and the second cutting portion is rotatable about the tip away the first cutting portion.

6. The surgical device of claim 1, wherein the second cutting portion is bi-directionally rotatable about the tip.

7. The surgical device of claim 1, wherein the tip includes a stiff transition element having a cut-out to permit the cutting portions to extend therethrough.

8. A surgical device comprising:
an elongated body having a proximal end and a distal end and a control collar;
a conical tip disposed at the distal end of the elongated body; and
a cutting unit having a first cutting portion and a second cutting portion, the first cutting portion and the second cutting portion being moveable in a longitudinal direction relative to the elongated body and to one another from a first position substantially proximal of the conical tip to a second position distal of the conical tip to capture a blood vessel between the first cutting portion and the second cutting portion, and at least one of the first or second cutting portions being rotatable relative to another of the first or second cutting portions circumferentially about the tip to cut the captured blood vessel,
wherein the first cutting portion has a sharpened edge and an edge of the second cutting portion facing the sharpened edge of the first cutting portion is flat.

9. The surgical device of claim 8, wherein the first cutting portion and the second cutting are configured to be energized for sealing, cutting or both of the captured blood vessel.

10. The surgical device of claim 8, wherein the first cutting portion is stationary and the second cutting portion is rotatable about the tip.

11. The surgical device of claim 8, wherein the second cutting portion is bi-directionally rotatable about the tip.

12. The surgical device of claim 8, wherein the first cutting portion and the second cutting portion are moveable in the longitudinal direction relative to one another by about 3 mm to about 5 mm.

13. The surgical device of claim 8, wherein the tip includes a stiff transition element having a cut-out to permit the first and second cutting portions to extend therethrough.

14. The surgical device of claim 8, wherein the first cutting portion is disposed at a distal end of an outer tubular member and the second cutting portion is disposed at a distal end of a inner tubular member slidably disposed within the outer tubular member.

15. The surgical device of claim 14, wherein an inner member adapter is connected to a proximal end of the outer tubular member by a compressible element, and the inner tubular member is coupled to the inner member adapter to enable longitudinal movement of the inner tubular element with respect to the outer tubular element.

* * * * *